United States Patent
Ruane et al.

(10) Patent No.: US 9,474,833 B2
(45) Date of Patent: Oct. 25, 2016

(54) STENT GRAFT WITH RELEASABLE THERAPEUTIC AGENT AND SOLUBLE COATING

(75) Inventors: Patrick H. Ruane, Hayward, CA (US);
Priscilla Reyes, Duncan, OK (US);
Blayne A. Roeder, Lafayette, IN (US);
Amy M. Vibbert, Avon, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 2200 days.

(21) Appl. No.: 11/958,090

(22) Filed: Dec. 17, 2007

(65) Prior Publication Data

US 2008/0167724 A1 Jul. 10, 2008

Related U.S. Application Data

(60) Provisional application No. 60/875,477, filed on Dec. 18, 2006.

(51) Int. Cl.
| | | |
|---|---|---|
| *A61F 2/04* | (2013.01) | |
| *A61F 2/06* | (2013.01) | |
| *A61L 31/10* | (2006.01) | |
| *A61L 31/16* | (2006.01) | |

(52) U.S. Cl.
CPC .............. *A61L 31/10* (2013.01); *A61L 31/16* (2013.01); *A61L 2300/416* (2013.01); *A61L 2300/602* (2013.01)

(58) Field of Classification Search
USPC ................ 623/1.13, 1.42, 1.43, 1.46, 23.7
See application file for complete search history.

(56) References Cited

U.S. PATENT DOCUMENTS

| | | | |
|---|---|---|---|
| 2,900,644 A | 8/1959 | Rosenberg et al. | ............. 3/1 |
| 3,562,352 A | 2/1971 | Nyilas et al. | ......... 260/824 |
| 3,562,820 A | 2/1971 | Braun | |
| 3,700,380 A | 10/1972 | Kitrilakis | ............. 3/1 |
| 3,789,828 A | 2/1974 | Schulte | ......... 128/1 R |
| 3,862,452 A | 1/1975 | Wichterle et al. | ............. 3/1 |
| 3,975,350 A | 8/1976 | Hudgin et al. | ....... 260/30.4 N |
| 4,131,604 A | 12/1978 | Szycher | ............ 528/79 |
| 4,173,689 A | 11/1979 | Lyman et al. | ............ 521/64 |
| 4,304,010 A | 12/1981 | Mano | ............. 3/1.4 |

(Continued)

FOREIGN PATENT DOCUMENTS

| | | |
|---|---|---|
| EP | 1 084 721 A2 | 3/2001 |
| WO | WO 00/10622 A1 | 3/2000 |

(Continued)

OTHER PUBLICATIONS

Machan, L.; "Clinical experience and applications of drug-eluting stents in the noncoronary vasculature, bile duct and esophagus"; Advanced Drug Delivery Reviews 58 (2006); pp. 447-462.

(Continued)

*Primary Examiner* — Yashita Sharma
(74) *Attorney, Agent, or Firm* — Brinks Gilson & Lione

(57) ABSTRACT

Medical devices for implantation within a body vessel comprising a graft material and a releasable therapeutic agent are provided. The graft material preferably comprises a biocompatible polyurethane and a therapeutic agent. Preferably, the medical device is a stent graft formed by attaching a polyurethane graft material comprising an elutable taxane therapeutic agent to a radially expandable frame.

20 Claims, 8 Drawing Sheets

(56) References Cited

U.S. PATENT DOCUMENTS

| | | | |
|---|---|---|---|
| 4,306,318 A | 12/1981 | Mano et al. ................... 3/1.4 |
| 4,334,327 A | 6/1982 | Lyman et al. ..................... 3/1 |
| 4,355,426 A | 10/1982 | MacGregor ..................... 3/1.4 |
| 4,459,252 A | 7/1984 | MacGregor ................ 264/46.9 |
| 4,604,762 A | 8/1986 | Robinson ......................... 623/1 |
| 4,623,347 A | 11/1986 | Kira ................................. 623/1 |
| 4,647,416 A | 3/1987 | Seiler, Jr. et al. ............ 264/118 |
| 4,675,361 A | 6/1987 | Ward, Jr. ....................... 525/92 |
| 4,678,468 A | 7/1987 | Hiroyoshi ........................ 623/1 |
| 4,687,482 A | 8/1987 | Hanson ............................ 623/1 |
| 4,695,281 A | 9/1987 | Miyata et al. .................. 623/11 |
| 4,731,073 A | 3/1988 | Robinson ......................... 623/1 |
| 4,743,258 A | 5/1988 | Ikada et al. ..................... 623/1 |
| 4,784,659 A | 11/1988 | Fleckenstein et al. ........... 623/1 |
| 4,816,339 A | 3/1989 | Tu et al. ....................... 428/421 |
| 4,828,561 A | 5/1989 | Woodroof ......................... 623/8 |
| 4,861,830 A | 8/1989 | Ward, Jr. ....................... 525/92 |
| 4,892,544 A | 1/1990 | Frisch ............................. 623/11 |
| 4,957,508 A | 9/1990 | Kaneko et al. ................. 623/12 |
| 4,996,054 A | 2/1991 | Pietsch et al. ................ 424/422 |
| 5,017,664 A | 5/1991 | Grasel et al. ................. 525/424 |
| 5,019,090 A | 5/1991 | Pinchuk ......................... 606/194 |
| 5,100,422 A | 3/1992 | Berguer et al. .............. 606/151 |
| 5,104,400 A | 4/1992 | Berguer et al. ............... 264/132 |
| 5,108,424 A | 4/1992 | Hoffman, Jr. et al. ........... 623/1 |
| 5,116,360 A | 5/1992 | Pinchuk et al. .................. 623/1 |
| 5,126,181 A | 6/1992 | Figuly et al. .................. 428/64 |
| 5,152,782 A | 10/1992 | Kowligi et al. ................ 623/1 |
| 5,227,043 A * | 7/1993 | Shakushiro et al. .......... 204/421 |
| 5,274,074 A | 12/1993 | Tang et al. ..................... 528/370 |
| 5,298,276 A | 3/1994 | Jayaraman ....................... 427/2 |
| 5,330,782 A | 7/1994 | Kanazawa ................... 427/2.25 |
| 5,412,068 A | 5/1995 | Tang et al. ..................... 528/370 |
| 5,486,593 A | 1/1996 | Tang et al. ..................... 528/370 |
| 5,575,815 A | 11/1996 | Slepian et al. ..................... 623/1 |
| 5,589,563 A | 12/1996 | Ward et al. ..................... 528/64 |
| 5,607,474 A | 3/1997 | Athanasiou et al. ........... 623/11 |
| 5,700,286 A | 12/1997 | Tartaglia et al. .................. 623/1 |
| 5,713,907 A | 2/1998 | Hogendijk et al. ........... 606/108 |
| 5,735,897 A | 4/1998 | Buirge ............................ 623/12 |
| 5,741,333 A | 4/1998 | Frid ................................ 623/12 |
| 5,769,884 A | 6/1998 | Solovay ........................... 623/1 |
| 5,779,729 A | 7/1998 | Severini ......................... 606/191 |
| 5,782,907 A | 7/1998 | Frantzen et al. ................... 623/1 |
| 5,855,598 A | 1/1999 | Pinchuk ............................ 623/1 |
| 5,861,033 A | 1/1999 | Martakos et al. .............. 623/11 |
| 5,863,627 A | 1/1999 | Szycher et al. ............. 428/36.8 |
| 5,891,558 A | 4/1999 | Bell et al. ..................... 428/218 |
| 5,948,875 A | 9/1999 | Liu et al. ....................... 528/61 |
| 5,980,564 A | 11/1999 | Stinson ............................ 623/1 |
| 5,984,965 A | 11/1999 | Knapp et al. .................. 623/12 |
| 6,013,099 A | 1/2000 | Dinh et al. ........................ 623/1 |
| 6,015,431 A | 1/2000 | Thornton et al. ................. 623/1 |
| 6,042,605 A | 3/2000 | Martin et al. ..................... 623/1 |
| 6,083,257 A | 7/2000 | Taylor et al. ..................... 623/1 |
| 6,096,070 A | 8/2000 | Ragheb et al. ................... 623/1 |
| 6,099,562 A | 8/2000 | Ding et al. ................... 623/1.46 |
| 6,156,064 A | 12/2000 | Chouinard .................... 623/1.44 |
| 6,177,523 B1 | 1/2001 | Reich et al. .................. 525/459 |
| 6,197,051 B1 | 3/2001 | Zhong .......................... 623/1.46 |
| 6,225,435 B1 | 5/2001 | Ito et al. ......................... 528/76 |
| 6,241,774 B1 | 6/2001 | Shimizu ..................... 623/23.64 |
| 6,254,642 B1 | 7/2001 | Taylor ......................... 623/23.64 |
| 6,264,700 B1 | 7/2001 | Kilcoyne et al. .......... 623/23.68 |
| 6,299,604 B1 | 10/2001 | Ragheb et al. ................. 604/265 |
| 6,302,917 B1 | 10/2001 | Dua et al. .................. 623/23.68 |
| 6,309,413 B1 | 10/2001 | Dereume et al. ............ 623/1.13 |
| 6,443,980 B1 | 9/2002 | Wang et al. |
| 6,515,016 B2 | 2/2003 | Hunter .......................... 514/449 |
| 6,730,064 B2 | 5/2004 | Ragheb et al. ................. 604/265 |
| 6,918,929 B2 * | 7/2005 | Udipi et al. .................. 623/1.42 |
| 6,939,377 B2 | 9/2005 | Jayaraman et al. ......... 623/1.46 |
| 7,060,319 B2 | 6/2006 | Fredrickson ................. 427/2.24 |
| 7,063,884 B2 | 6/2006 | Hossainy et al. ............. 428/212 |
| 7,202,325 B2 | 4/2007 | Pacetti et al. ................ 528/272 |
| 7,214,759 B2 | 5/2007 | Pacetti et al. ................ 528/190 |
| 7,285,304 B1 | 10/2007 | Hossainy et al. ............ 427/2.24 |
| 2001/0002444 A1 | 5/2001 | Zilla et al. ................... 623/1.39 |
| 2001/0014717 A1 | 8/2001 | Hossainy et al. .............. 525/60 |
| 2001/0049550 A1 | 12/2001 | Martin et al. ................ 623/1.13 |
| 2002/0032414 A1 | 3/2002 | Ragheb et al. ................. 604/265 |
| 2003/0093141 A1 * | 5/2003 | Dimatteo et al. ............ 623/1.13 |
| 2004/0034407 A1 | 2/2004 | Sherry .......................... 623/1.15 |
| 2004/0047909 A1 | 3/2004 | Ragheb et al. ............... 424/471 |
| 2004/0098106 A1 | 5/2004 | Williams et al. ............. 623/1.15 |
| 2004/0117007 A1 | 6/2004 | Whitbourne et al. ........ 623/1.42 |
| 2004/0142015 A1 | 7/2004 | Hossainy et al. ............. 424/423 |
| 2004/0162609 A1 | 8/2004 | Hossainy et al. ............ 623/1.42 |
| 2004/0170752 A1 | 9/2004 | Luthra et al. ................ 427/2.24 |
| 2004/0219214 A1 | 11/2004 | Gravett et al. ................ 424/484 |
| 2004/0225077 A1 | 11/2004 | Gravett et al. ................ 525/418 |
| 2004/0254419 A1 | 12/2004 | Wang et al. ...................... 600/8 |
| 2004/0260318 A1 * | 12/2004 | Hunter et al. ................. 606/153 |
| 2005/0025797 A1 | 2/2005 | Wang et al. .................. 424/422 |
| 2005/0025803 A1 | 2/2005 | Richard et al. |
| 2005/0079132 A1 | 4/2005 | Wang et al. .................. 424/1.11 |
| 2005/0187376 A1 | 8/2005 | Pacetti ......................... 528/425 |
| 2005/0220835 A1 | 10/2005 | Jayaraman et al. .......... 424/423 |
| 2005/0233062 A1 | 10/2005 | Hossainy et al. ............. 427/2.1 |
| 2005/0265960 A1 | 12/2005 | Pacetti et al. .............. 424/78.36 |
| 2005/0281883 A1 | 12/2005 | Daniloff et al. .............. 424/489 |
| 2005/0288481 A1 | 12/2005 | DesNoyer et al. ........... 528/310 |
| 2006/0020329 A1 * | 1/2006 | Raze et al. .................. 623/1.42 |
| 2006/0047095 A1 | 3/2006 | Pacetti .......................... 526/242 |
| 2006/0062821 A1 | 3/2006 | Simhambhatla et al. .... 424/422 |
| 2006/0067908 A1 | 3/2006 | Ding ......................... 424/78.27 |
| 2006/0111546 A1 | 5/2006 | Pacetti et al. ................ 528/190 |
| 2006/0115513 A1 | 6/2006 | Hossainy et al. ............. 424/423 |
| 2006/0135963 A1 | 6/2006 | Kick et al. .................... 606/108 |
| 2006/0147412 A1 | 7/2006 | Hossainy et al. .......... 424/78.27 |
| 2006/0149365 A1 | 7/2006 | Fifer et al. .................... 623/1.46 |
| 2006/0160985 A1 | 7/2006 | Pacetti et al. ................ 528/272 |
| 2006/0240065 A1 | 10/2006 | Chen .............................. 424/423 |
| 2006/0246109 A1 | 11/2006 | Hossainy et al. ............. 424/426 |
| 2006/0269586 A1 | 11/2006 | Pacetti .......................... 424/423 |
| 2007/0003589 A1 | 1/2007 | Astafieva et al. ............ 424/423 |
| 2007/0009565 A1 | 1/2007 | Pacetti et al. ................. 424/423 |
| 2007/0010702 A1 | 1/2007 | Wang et al. ...................... 600/8 |
| 2007/0167602 A1 | 7/2007 | Pacetti et al. ................ 528/190 |
| 2007/0196420 A1 | 8/2007 | Dwyer .......................... 424/423 |
| 2007/0202323 A1 | 8/2007 | Kleiner et al. ................ 428/336 |
| 2007/0228345 A1 | 10/2007 | Pacetti .......................... 252/601 |
| 2007/0293941 A1 | 12/2007 | Gale et al. ................... 623/1.38 |

FOREIGN PATENT DOCUMENTS

| | | | |
|---|---|---|---|
| WO | WO 01/49268 A1 | 7/2001 |
| WO | WO 02/15951 A2 | 2/2002 |
| WO | WO 02/058753 A2 | 8/2002 |

OTHER PUBLICATIONS

International Search Report mailed May 15, 2009 for International Application No. PCT/US2007/025665.

Written Opinion mailed May 15, 2009 for International Application No. PCT/US2007/025665.

* cited by examiner

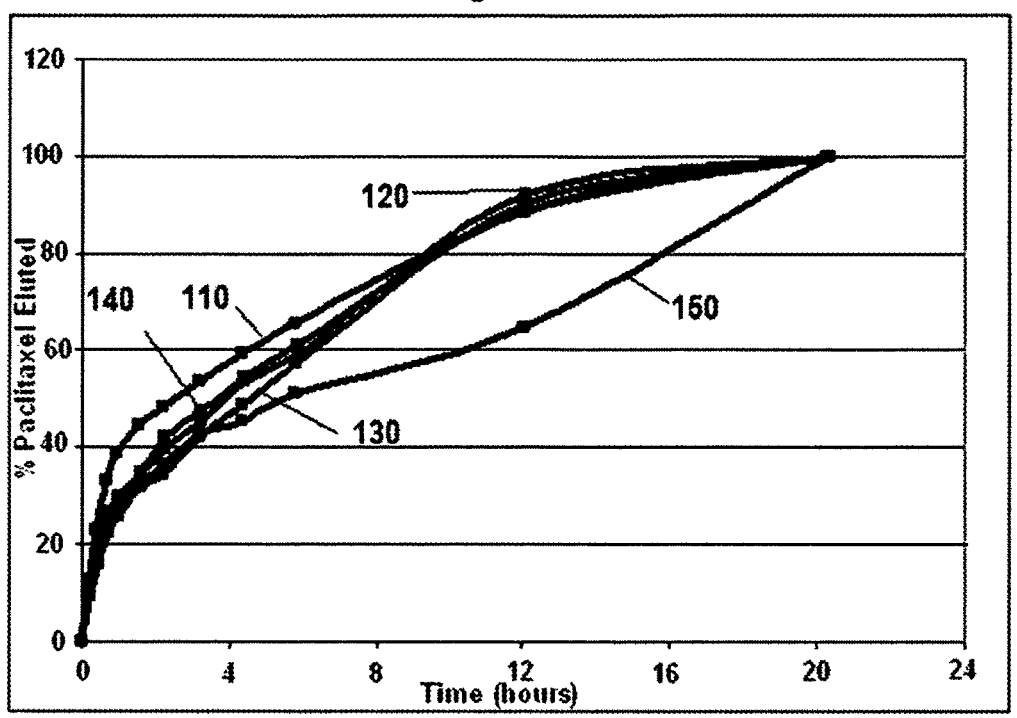

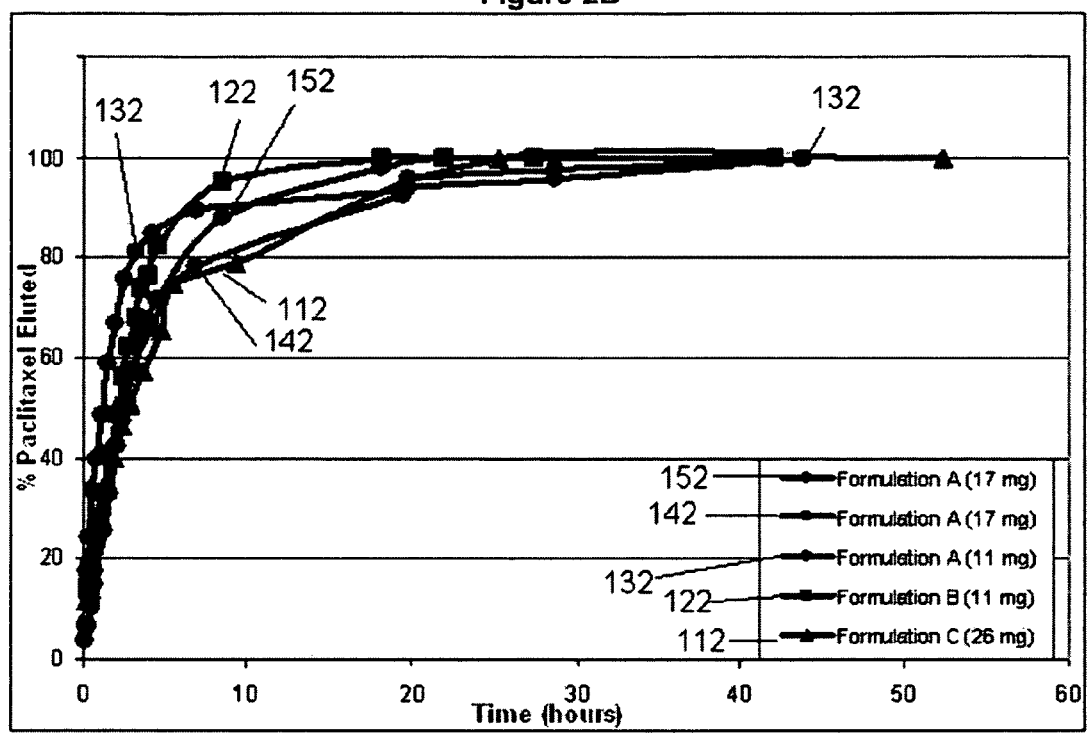

STENT GRAFT WITH RELEASABLE THERAPEUTIC AGENT AND SOLUBLE COATING

RELATED APPLICATIONS

This application claims the benefit of U.S. Provisional Patent Application 60/875,477, filed Dec. 18, 2006 and entitled "STENT GRAFT WITH RELEASABLE THERAPEUTIC AGENT AND SOLUBLE COATING," which is incorporated herein by reference in its entirety.

TECHNICAL FIELD

The present invention relates to medical devices for implantation in a body vessel. More particularly, the present invention relates to implantable medical devices adapted to release a therapeutic agent, and methods for manufacturing the same.

BACKGROUND

Various implantable medical devices are advantageously inserted within various body vessels to treat various conditions. Minimally invasive techniques and instruments for placement of intraluminal medical devices, such as stent grafts, have been developed to treat and repair undesirable conditions within body vessels, including treatment of conditions that affect fluid flow within a body vessel.

Biliary tract cancers, also called cholangiocarcinomas, refer to malignancies occurring in the organs of the biliary system, including pancreatic cancer, gallbladder cancer, and cancer of bile ducts. In the United States, an estimated 20,000 new cases of liver and biliary tract cancer are diagnosed annually. Biliary tract cancer is the second most common primary hepatobiliary cancer, after hepatocellular cancer. Approximately 7,500 new cases of biliary tract cancer are diagnosed each year; about 5,000 of these are gallbladder cancer, and between 2,000 and 3,000 are bile duct cancers.

Tumor growth may obstruct the body vessels, such as biliary ducts. For example, the biliary system, which drains bile from the liver into the duodenum, may be obstructed by (1) a tumor composed of bile duct cells (cholangiocarcinoma), (2) a tumor which invades the bile duct (e.g., pancreatic carcinoma), or (3) a tumor which exerts extrinsic pressure and compresses the bile duct (e.g., enlarged lymph nodes). One example of primary biliary tumors are adenocarcinoma (which are also called Klatskin tumors when found at the bifurcation of the common hepatic duct). These tumors are also referred to as biliary carcinomas, choledocholangio-carcinomas, or adenocarcinomas of the biliary system. Benign tumors which affect the bile duct (e.g., adenoma of the biliary system), and, in rare cases, squamous cell carcinomas of the bile duct and adenocarcinomas of the gallbladder, may also cause compression of the biliary tree and therefore, result in biliary obstruction. Tumor overgrowth of the common bile duct results in progressive cholestatic jaundice.

Most of the tumors from the pancreas arise from cells of the pancreatic ducts. This is a highly fatal form of cancer (5% of all cancer deaths; 26,000 new cases per year in the U.S.) with an average of 6 months survival and a 1 year survival rate of only 10%. When these tumors are located in the head of the pancreas they frequently cause biliary obstruction, and this detracts significantly from the quality of life of the patient. While all types of pancreatic tumors are generally referred to as "carcinoma of the pancreas" there are histologic subtypes including: adenocarcinoma, adenosquamous carcinoma, cystadeno-carcinoma, and acinar cell carcinoma. Hepatic tumors, may also cause compression of the biliary tree, and therefore cause obstruction of the biliary ducts.

Implantable medical devices may be used to maintain body vessel patency while delivering a therapeutic agent proximate the site of implantation. For example, stent grafts may be configured for insertion in a biliary or pancreatic body vessel. Intraluminal medical devices can be deployed in a body vessel at a point of treatment and the delivery device subsequently withdrawn from the vessel, while the medical device is retained within the vessel to provide sustained improvement in vascular valve function or to increase vessel patency.

Both primary biliary tumors, as well as other tumors which cause compression of the biliary tree, may be treated by implanting a stent graft configured to release a therapeutic agent. The stent graft may further comprise a releasable therapeutic agent within the body vessel to treat a disease condition, such as a localized tumor, proximate an implantation site. A releasable therapeutic agent may be combined with a stent graft, or other implantable medical devices, in various ways, including: (a) by directly affixing the therapeutic agent to the implant or device (e.g., by either spraying the implant or device with a polymer/drug film, or by dipping the implant or device into a polymer/drug solution, or by other covalent or noncovalent means); (b) by coating the implant or device with a substance such as a hydrogel which will in turn absorb the therapeutic agent; (c) by interweaving a therapeutic agent-coated thread (or the polymer itself formed into a thread) into the medical device; (d) by inserting the medical device into a sleeve or mesh which comprises or is coated with the therapeutic agent; (e) constructing the medical device itself with the therapeutic agent; or (f) by otherwise adapting the medical device to release the therapeutic agent. For example, published U.S. patent application no. US2005/0220835 A1 by Jayaraman et al., filed Mar. 30, 2004, discloses implantable medical devices comprising a polyetherurethane modified by admixture with a siloxane surface modifying additive in combination with a releasable therapeutic agent.

One or more intraluminal medical devices can be introduced to a point of treatment within a body vessel using a delivery catheter device passed through the vasculature communicating between a remote introductory location and the implantation site, and released from the delivery catheter device at the point of treatment within the body vessel. Radially expandable stent grafts comprising a releasable therapeutic agent in the graft material are typically radially compressed to a low-profile configuration and inserted into a delivery catheter system. The stent grafts may be configured for expansion within a body vessel by balloon expansion or self-expansion. Once expanded, the stent grafts may resist radial compression. Failure of the graft material to radially compress to a desired radial profile may result in undesirable levels of friction on the graft material when loading the stent graft into the delivery catheter. Undesirable levels of friction on the stent graft may compromise the mechanical integrity of the graft or reduce retention of the therapeutic agent within the device, compromising the therapeutic effectiveness of the device.

What is needed are implantable stent grafts comprising a therapeutically effective amount of a releasable therapeutic agent that are configured to withstand radial compression without undesirably compromising the integrity of the stent graft or loading of the therapeutic agent. Also needed are stent grafts providing a desirably sustained release of the therapeutic agent.

SUMMARY

Implantable medical devices comprising a releasable therapeutic agent are provided herein, as well as related methods of manufacture and methods of treatment. The implantable medical devices may be configured as stent grafts comprising a radially expandable support frame combined with a synthetic graft material containing the releasable therapeutic agent. In one preferred embodiment, stent grafts may be configured to release a therapeutic agent at a slower rate as the concentration of the therapeutic agent in the graft material is increased. In another embodiment, preferred stent grafts may be configured to release the therapeutic agent more slowly at temperatures approaching body temperature (e.g., 37° C.) than at temperatures below body temperature (e.g., 25° C.) or above body temperature (e.g., 60° C.), so as to provide a sustained release of the therapeutic agent within a body vessel after implantation. For example, increasing the temperature of a preferred graft material from 25° C. to 37° C. may increase the time required to elute 80% of the taxane therapeutic agent by weight from the graft material in vitro in a 0.5% aqueous SDS solution.

Other embodiments provide for a stent graft adapted to release a therapeutic agent at a slower rate by increasing the amount of the therapeutic agent in the stent graft and releasing the therapeutic agent at a slower rate at or near body temperature (e.g., upon implantation) than at room temperature (e.g., before implantation). By allowing for increased loading of the therapeutic agent into the graft material and/or slowing the rate of release as a function of increasing the amount of therapeutic agent and/or achieving temperatures at or near human body temperature, certain preferred embodiments described herein may provide a sustained release of therapeutic agents such as paclitaxel within a body vessel. For example, conditions such as biliary tumors may be treated by implanting one or more stent grafts configured to release paclitaxel over a desirably sustained period of time. For example, increasing the total amount of the taxane therapeutic agent in a preferred graft material may increase the time required to elute 80% of the taxane therapeutic agent by weight from the graft material in vitro in a 0.5% aqueous SDS solution at 25° C.

The stent graft medical devices preferably include a graft material containing the therapeutic agent and a support frame attached to the graft material. The support frame is typically a self-expanding cylindrical device including a series of sinusoidal ring members formed from interconnected struts and bends defining plurality of openings between an external (abluminal) side or surface and an interior (luminal) side or surface defining a substantially cylindrical lumen. The graft material is attached to the support frame to form a stent graft structure. Preferably, the synthetic graft material is formed from two or more layers of a biocompatible polymeric material disposed on the abluminal and luminal sides of the support frame. In addition, the stent graft medical device may include a coating of a lubricious polymer on the abluminal surface of the device. For example, stent graft structures are provided wherein a graft material including a graft polymer of polyurethane is attached to a support frame and is configured to release a therapeutic agent. The graft material such as polyurethane may more readily adhere to itself than to a support frame formed from a material such as stainless steel or a nickel-titanium alloy. Therefore, in one preferred aspect, the stent graft includes a first layer of the graft material contacting the abluminal side of the support frame attached directly to a second layer of the graft material contacting the luminal side of the support frame through the plurality of holes in the support frame.

The stent graft is preferably adapted for implantation within a body vessel for delivery of a therapeutic agent over a desired time period. In one aspect, the stent graft is configured to release a chemotherapeutic agent, such as a taxane therapeutic agent, within a body vessel proximate to a carcinogenic site, such as a biliary tract tumor. Desirably, the stent graft contains a therapeutically effective amount of the chemotherapeutic agent. The therapeutic agent is preferably contained within one or more layers of the graft material. For example, stent grafts configured to release a taxane therapeutic agent may include a multi-layer polyurethane graft material containing a taxane therapeutic agent at a dose of at least about 3 micrograms per $mm^2$ of abluminal surface area of the graft material, and more preferably doses of about 0.1-100 micrograms of a therapeutic agent per $mm^2$ of abluminal surface area. The graft material may include a graft polymer; preferably a polyetherurethane modified with a siloxane surface modifying additive. The graft material comprising the graft polymer and the therapeutic agent preferably releases the therapeutic agent within a body vessel over a desired treatment period, such as about 6 months or longer. The stent graft may be configured for radial compression to a suitable diameter for delivery to a body vessel from a delivery system comprising a catheter. The catheter can be adapted to move along a wire guide through a body vessel to a point of treatment, where the radially compressed stent graft may be radially expanded.

The abluminal surface of the graft material preferably includes a lubricious polymer in the form of a coating to promote crimping of the stent graft to a suitably low radial profile for loading into the delivery system. The lubricious polymer can include a water soluble polymer such as polyethylene glycol (PEG). Preferably, the stent graft is adapted to assume a radially compressed configuration suitable for delivery from a delivery catheter having a diameter of less than 20-french, and preferably about 15-, 10-, 9-, 8-, 7- or 6-french. The lubricious polymer coating is preferably configured to permit loading of the stent graft into the delivery system without undesirably compromising the subsequent release of the therapeutic agent upon implantation. Typically, the lubricious polymer coating reduces frictional forces on the graft during insertion of the stent graft into a delivery catheter, while being readily soluble in water and is rapidly dissolved within the body vessel. Most preferably, the weight ratio of the therapeutic agent to the lubricious polymer is about 3.50 or lower, such as ratios between about 0.10 and 3.50 and most preferably about 0.10 to 1.50.

In one embodiment, a stent graft structure includes a therapeutically effective dose of a therapeutic agent. For example, a stent graft may include about 1-100 micrograms of taxane therapeutic agent per $mm^2$ of abluminal stent graft area within the graft material. Suitable amounts of the taxane therapeutic agent may include, for example, ranges of about 10-90, 20-70, 40-60, 10-25, 10-20 and 10-15 micrograms of a taxane therapeutic agent per $mm^2$ in a graft material. In addition to the therapeutic agent, the graft material may include a biocompatible polyurethane or polyurethand derivative such as modified polyurethane-based polymer (e.g., a polyureaurethane). The graft material is preferably configured to provide a desirable sustained release of the taxane therapeutic agent. In particular, sustained release rates characterized by a release of up to about 80% by weight of the taxane therapeutic agent over a period of about 100 hours (about 40 days) may be obtained. Most preferably, the sustained release stent graft configurations include a lubricious polymer coating with a weight ratio of the taxane therapeutic agent to the lubricious polymer of about 3.50 or lower, such as ratios between about 0.10 and 3.50 and most preferably about 0.10 to 1.50.

BRIEF DESCRIPTION OF THE DRAWINGS

FIG. 2A shows the elution of paclitaxel from various five-layer stent grafts containing a releasable paclitaxel therapeutic agent at room temperature.

FIG. 2B shows the elution of paclitaxel from various stent grafts containing a releasable paclitaxel therapeutic agent at room temperature.

DETAILED DESCRIPTION

Figure 1A:
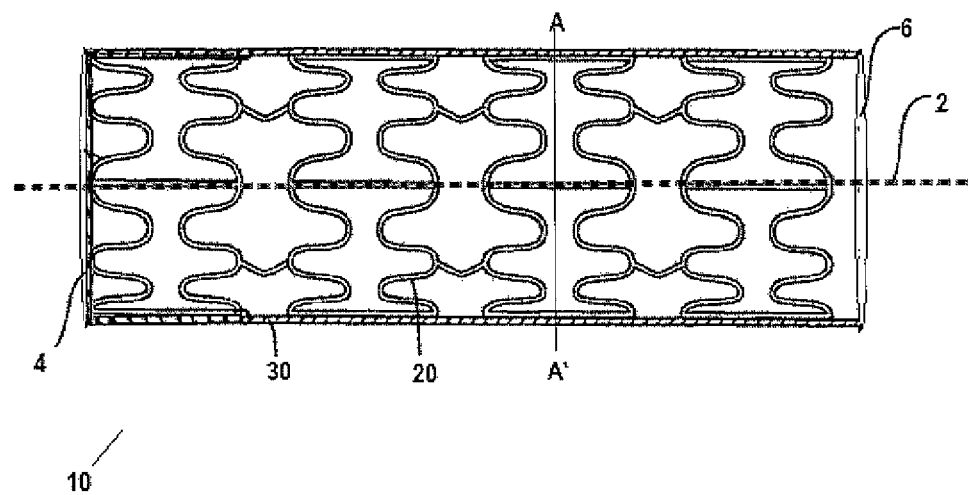
FIG. 1A is a side view of a self-expanding implantable stent graft in a radially expanded state.

The following detailed description and appended drawings describe and illustrate various exemplary embodiments of the invention. The description and drawings serve to enable one skilled in the art to make and use the invention.

1. Definitions

As used herein the terms "comprise(s)," "include(s)," "having," "has," "contain(s)," and variants thereof, are intended to be open-ended transitional phrases, terms, or words that do not preclude the possibility of additional acts or structure.

As used herein, the term "implantable" refers to an ability of a medical device to be positioned at a location within a body, such as within a body vessel. Furthermore, the terms "implantation" and "implanted" refer to the positioning of a medical device at a location within a body, such as within a body vessel.

Unless otherwise indicated, as used herein, a "layer" refers to a portion of a structure having a defined composition or structure and a defined boundary with respect to an adjacent material. A layer of a graft material may be deposited by spray deposition of a polymer solution in multiple spray deposition events. For example, a single layer may be formed by deposition of material in separate portions, where no definite boundary of structure or composition is present between the material deposited in the first and subsequent portions. Furthermore, a single layer may be formed by spray deposition of a first portion of a deposited material followed by drying of the deposited material and subsequent spray deposition of a second portion of material with the same composition onto the dried deposited material, provided that the deposited material does not include a structural or compositional boundary between the first deposited material and the second deposited material.

The term "hydrophobic," as used herein, refers to a substance with a solubility in water of less than 0.1 mg/mL at room temperature (about 25° C.).

The term "elution," as used herein, refers to removal of a material from a substrate by means of an elution medium. The elution medium can remove the material from the substrate by any process, including by acting as a solvent with respect to the removable material. For example, in medical devices adapted for introduction to the vascular system, blood can act as an elution medium that dissolves a therapeutic agent releasably associated with a portion of the surface of the medical device. The removable material preferably includes the therapeutic agent, but can also include a bioabsorbable elastomer. The therapeutic agent can be selected to have a desired solubility in a particular elution medium. Unless otherwise indicated, the term "release" referring to the removal of the therapeutic agent from a coating in contact with an elution medium is intended to be synonymous with the term "elution" as defined above. Similarly, an "elution profile" is intended to be synonymous with a "release profile," unless otherwise indicated.

An "elution medium," as used herein, refers to a condition or environment that releases a therapeutic agent from a coating upon contact of the coating with the elution medium for a desired period of time. A suitable elution medium is any substance or environment into which the therapeutic agent can be released in vivo or in vitro. The elution medium is desirably a fluid. More desirably, the elution medium is a biological fluid such as blood or porcine serum, although any other chemical substance can be used as an elution medium. For example, elution media for in vitro testing may include phosphate buffered saline, blood, SDS, aqueous solutions, reaction conditions including temperature and/or pH, or combinations thereof, that release the therapeutic agent at a desired rate. Preferably, the elution medium is a fluid that provides an elution profile that is similar to the elution profile obtained upon implantation of the medical device within a body vessel. For example, porcine serum can provide an elution profile that is similar to the elution profile in blood for some coating configurations.

The term "luminal surface" or "luminal side," as used herein, refers to the portion of the surface area of a medical device defining at least a portion of an interior lumen. Conversely, the term "abluminal surface" or "abluminal side," as used herein, refers to portions of the surface area of a medical device that do not define at least a portion of an interior lumen. For example, where the medical device is a tubular frame formed from a plurality of interconnected struts and bends defining a cylindrical lumen, the abluminal surface can include the exterior surface, sides and edges of the struts and bends, while the luminal surface can include the interior surface of the struts and bends.

As used herein, "endolumenally," "intraluminally" or "transluminal" all refer synonymously to implantation placement by procedures wherein the prosthesis is advanced within and through the lumen of a body vessel from a remote location to a target site within the body vessel. In vascular procedures, a medical device will typically be introduced "endovascularly" using a catheter over a wire guide under fluoroscopic guidance. The catheters and wire guides may be introduced through conventional access sites to the vascular system.

As used herein, the term "body vessel" means any body passage lumen that conducts fluid, including but not limited to blood vessels, esophageal, intestinal, biliary, urethral and ureteral passages.

Any concentration ranges, percentage range, or ratio range recited herein are to be understood to include concentrations, percentages or ratios of any integer within that range and fractions thereof, such as one tenth and one hundredth of an integer, unless otherwise indicated. Also, any number range recited herein relating to any physical feature, such as polymer subunits, size or thickness, are to be understood to include any integer within the recited range, unless otherwise indicated. It should be understood that the terms "a" and "an" as used above and elsewhere herein refer to "one or more" of the enumerated components. For example, "a" polymer refers to one polymer or a mixture comprising two or more polymers.

The term "alloy" refers to a substance composed of two or more metals or of a metal and a nonmetal intimately united, for example by chemical or physical interaction. Alloys can be formed by various methods, including being fused together and dissolving in each other when molten, although molten processing is not a requirement for a material to be within the scope of the term "alloy." As understood in the art, an alloy will typically have physical or chemical properties that are different from its components.

The term "mixture" refers to a combination of two or more substances in which each substance retains its own chemical identity and properties.

The terms "frame" and "support frame" are used interchangeably herein to refer to a structure that can be implanted, or adapted for implantation, within the lumen of a body vessel.

2. Medical Device Configurations

In a first embodiment, the present disclosure describes implantable medical devices for placement within a body passage. Preferably, the medical device is configured as a stent graft including a radially expandable support frame attached to a graft material. The stent graft may include a support frame joined to a tubular graft material that includes a releasable therapeutic agent. Preferably, the graft material is configured to release the therapeutic material from the abluminal (outer) surface of the stent graft upon implantation within a body vessel. Most preferably, the graft material is configured to release a therapeutically effective dose of the therapeutic agent (e.g., 3-5, 3-7, 3-12 or 3-20 micrograms paclitaxel per $mm^2$ of abluminal surface area).

Typically, the support frame has a cylindrical shape formed by a plurality of longitudinally-aligned sinusoidal ring members attached to a tubular graft material containing a releasable therapeutic agent. Referring to FIG. 1A, a stent graft 10 includes a support frame 20 attached to a tubular graft material 30. The support frame 20 is formed by eight self-expanding sinusoidal ring members axially aligned around a longitudinal axis 2 to form a cylindrical shape. The sinusoidal ring members are optionally joined by longitudinal struts. The tubular graft material 30 is attached to the support frame 20 to define a fluid-conducting enclosed lumen 6 centered along the longitudinal axis 2.

Figure 1B:
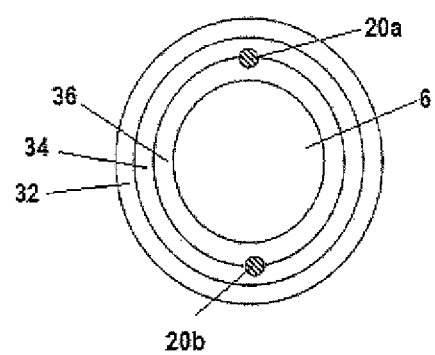
FIG. 1B is a cross sectional view along the line A-A' shown in FIG. 1A.

The graft material 30 preferably encloses the support frame 20. FIG. 1B is a lateral cross section along the line A-A' of the medical device 10 shown in FIG. 1A. The graft material 30 preferably includes an inner portion 36 positioned on the luminal side of the support frame 20, and an outer portion 34 positioned on the abluminal side of the support frame 20. The inner portion 36 refers the portion of the graft material 30 positioned on the luminal side of the center of the support frame 20; the outer portion 34 refers to the graft material 30 positioned on the abluminal side of the center of the support frame 20. Support frame portions 20a, 20b may be positioned in the middle of a single layer of the graft material 30, or between two layers of the graft material 30. Preferably, the graft material 30 is formed by positioning the support frame 20 around the inner portion 36 of the graft material 30 and then contacting the outer portion 34 of the graft material with the abluminal surface of the support frame 20 under conditions that join the inner portion 36 and the outer portion 34 of the graft material 30 to each other through openings in the support frame 20. The inner portion 36 and the outer portion 34 of the graft material 30 may have the same or different compositions or structures, and may form portions of a single layer or form separate layers. Optionally, the inner portion 36 and/or outer portion 34 of the graft material include multiple layers of material having different compositions and/or different structures.

The abluminal surface of the graft material 30 is preferably coated with a lubricious polymer to form a lubricious polymer coating 32 that reduces the frictional force on the graft material 30 during crimping and loading of the stent graft 10 into a delivery catheter. The lubricious polymer coating 32 may include any suitable material that does not undesirably alter the rate of release of the therapeutic agent from the graft material, while providing a desired level of friction reduction during the crimping and loading process. Preferably, the lubricious polymer coating 32 is a water-soluble polymer.

In one particular embodiment, a coated implantable medical device comprising a graft material configured to release a therapeutic agent is provided. The coated implantable medical device may comprise: a radially expandable support frame having one or more sinusoidal ring members; a graft material attached to the support frame, the graft material having an abluminal surface and a luminal surface defining a substantially cylindrical lumen, the graft material comprising a polyurethane and a polydimethylsiloxane surface modifying agent and a therapeutic agent; and a lubricious coating comprising poly(ethylene glycol) on the abluminal surface of the graft material.

3. Graft Materials

Graft material 30 can include a graft polymer. Preferably, the graft material 30 comprises one or more thromboresistant materials. The thromboresistant material is preferably a biocompatible polyurethane material optionally including a releasable bioactive agent. Preferably, the thromboresistant material is a biocompatible polyurethane material comprising a surface modifying agent, as described herein.

The thromboresistant material, as disclosed herein, can be selected from a variety of materials, but preferably comprises a biocompatible polyurethane material. Examples of preferred graft polymers used in graft materials 30 include the polyurethane materials described in U.S. patent application Ser. No. 11/494,424, filed Jul. 27, 2006 and entitled "IMPLANTABLE THROMBORESISTANT VALVE," as well as U.S. Provisional Patent Application Ser. No. 60/780,443, filed Mar. 8, 2006 and entitled "IMPLANTABLE THROMBORESISTANT VALVE," which are incorporated herein by reference in their entirety. One particularly preferred biocompatible polyurethane is THORALON (THORATEC, Pleasanton, Calif.), described in U.S. Pat. Application Publication No. 2002/0065552 A1 and U.S. Pat. No. 4,675,361, both of which are incorporated herein by reference. The biocompatible polyurethane material sold under the tradename THORALON is a polyurethane base polymer (referred to as BPS-215) blended with a siloxane containing surface modifying additive (referred to as SMA-300). The concentration of the surface modifying additive may be in the range of 0.5% to 5% by weight of the base polymer.

Biocompatible polyurethane polymers have been used in certain vascular applications and are characterized by thromboresistance, high tensile strength, low water absorption, low critical surface tension, and good flex life. For example, the biocompatible polyurethane material sold under the tradename THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial. The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference. The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

Biocompatible polyurethane polymers can be formed as non-porous material or as a porous material with varying degrees and sizes of pores, as described below. Implantable medical devices can comprise one or both forms of biocompatible polyurethane polymers. The thromboresistant material preferably comprises the non-porous form of the biocompatible polyurethane sold as THORALON. The porous forms of biocompatible polyurethane polymers can also be used as a thromboresistant material, but are preferably employed as an adhesion promoting region. For example, valve leaflets preferably comprise non-porous THORALON as a thromboresistant material, while adhesion promoting body vessel contact region on the outside of a prosthetic valve preferably comprise porous THORALON as an adhesion promoting material.

For example, porous biocompatible polyurethane polymerscan be formed as THORALON by mixing the polyetherurethane urea (BPS-215), the surface modifying additive (SMA-300) and a particulate substance in a solvent. The particulate may be any of a variety of different particulates or pore forming agents, including inorganic salts. Preferably the particulate is insoluble in the solvent. The solvent may include dimethyl formamide (DMF), tetrahydrofuran (THF), dimethyacetamide (DMAC), or dimethyl sulfoxide (DMSO), or mixtures thereof. The composition can contain from about less than 1 wt % to about 40 wt % polymer, and different levels of polymer within the range can be used to fine tune the viscosity needed for a given process. The composition can contain less than 5 wt % polymer for some spray application embodiments, such as 0.1-5.0 wt %. For dipping application methods, compositions desirably comprise about 5 to about 25 wt %. The particulates can be mixed into the composition. For example, the mixing can be performed with a spinning blade mixer for about an hour under ambient pressure and in a temperature range of about 18° C. to about 27° C. The entire composition can be cast as a sheet, or coated onto an article such as a mandrel or a mold. In one example, the composition can be dried to remove the solvent, and then the dried material can be soaked in distilled water to dissolve the particulates and leave pores in the material. In another example, the composition can be coagulated in a bath of distilled water. Since the polymer is insoluble in the water, it will rapidly solidify, trapping some or all of the particulates. The particulates can then dissolve from the polymer, leaving pores in the material. It may be desirable to use warm water for the extraction, for example water at a temperature of about 60° C. The resulting pore diameter can also be substantially equal to the diameter of the salt grains. The resulting void-to-volume ratio, as defined above, can be substantially equal to the ratio of salt volume to the volume of the polymer plus the salt. Formation of porous THORALON is described, for example, in U.S. Pat. Application Publication Nos. 2003/0114917 A1 and 2003/0149471 A1, both of which are incorporated herein by reference.

Preferably, the graft material is a blood-compatible polymer admixture comprising at least 95 volume % of a base polymer and no greater than 5 volume % of a solid polymer additive comprising a poly(dialkysiloxane) block chemically bonded to a polyurethane segment of from 1 to 10 repeating monomer units. The polymer additive may be dispersed throughout the base polymer. One widely accepted hypothesis regarding blood compatibility is that it is maximized within a narrow range of surface free energies, which give rise to favorable interactions with plasma proteins. A common measurement of such free energy is by Zisman's critical surface tension ($\gamma_c$ or "gamma sub-c"). The optimum value has been found empirically to lie within the range of about 20 to 30 dynes per centimeter. See Baeir, Ann. N.Y. Acad. Sci., 17, 282 (1967). The base polymer and polymer admixture may have a desirable free energy, $\gamma_c$, less than said base polymer, said polymer admixture being characterized by a $\gamma_c$ between about 10 to 35 dyne/cm. For biomedical applications, other characteristics of the base polymer are that it usually exhibits a critical surface tension ($\gamma_c$) in excess of that desirable for a blood contact surface and in excess of the polymer additive, and/or exhibits a contact angle hysteresis lower than desirable for a blood contact surface. As defined herein, $\gamma_c$ measurements are performed by the direct method using a contact angle meter of the Kernco or Rame-Hart type and a series of seven solvents according to the Zisman procedure as set forth in A. W. Adamson, Physical Chemistry for Surfaces, 339-357, 351 (3d Ed.). Measurements are made at room temperature using advancing angles on microscopically smooth solvent cast films annealed at 60° C. for at least four hours. The mean contact angles are fitted to a Zisman plot using a linear regression calculator program. The contact angle hysteresis measurements were made by the method set forth in Adamson, ibid., pp. 347-348. The $\gamma_c$ of the unmodified polyetherurethane is about 28 dyne/cm. The $\gamma_c$ of the polyetherurethane containing the block copolymer additive is preferably about 20 dyne/cm.

Particularly, graft materials comprising terpolymers of polyurethane/polyethyleneglycol/polydimethylsiloxane are preferred. These additives possess the very non-polar polydimethylsiloxane groups and the very polar polyethylene oxide groups, both of which may be used at a molecular weight that causes them to be above their glass transition temperatures and/or melting points at the use temperature of 37° C. The presence of both polar groups and non-polar groups in the additive is desirable for blood compatibility, but these groups should also be mobile enough at body temperature (or other temperatures at which they are used), in order to reorient or exchange places with one another according to the environment in which the surface is immersed.

In one example, the graft material may be a modified, solid polymer formed of a base polymer and a solid thermoplastic segmented block copolymer additive blended with said base polymer, said additive comprising an essentially linear segmented copolymer chain; said additive characterized by a $\gamma_c$ less than said base polymer and said segmented copolymer chain characterized by the presence of at least one polar hard segment having a glass transition temperature or crystalline melting temperature above 37° C., and a nonpolar soft block having a glass transition temperature below 37° C. said additive further comprising a second essentially linear polymer chain chemically bonded to said segmented copolymer chain, said second polymer chain being selected from a polar homopolymer or a second segmented copolymer, said second segmented copolymer or polar homopolymer characterized by the presence of at least one second polar hard segment having a glass transition temperature or crystalline melting temperature above 37° C., said polar hard segments independently selected from the group consisting of a polyurethane and a polyurethaneurea, and said second segmented copolymer further characterized by the presence of a polar soft block having a glass transition temperature or crystalline melting temperature below 37° C. Preferably, the base polymer is not a polycarbonate of 4,4'-diphenyldimethylmethane.

In another example, the graft material may comprise a modified solid polymer blend formed of a base polymer and a solid thermoplastic segmented block copolymer additive blended with said base polymer, said additive comprising a first essentially linear segmented copolymer chain and a second essentially linear polymer chain chemically bonded to said first segmented copolymer chain, said second polymer chain being selected from a polar homopolymer or a second segmented copolymer; said additive characterized by a $\gamma_c$ less than said base polymer and said first segmented copolymer chain characterized by the presence of at least one polar hard segment having a glass transition temperature or crystalline melting temperature above 37° C., and a nonpolar soft block having a glass transition temperature or crystalline melting temperature below 37° C.; said second segmented copolymer or polar homopolymer characterized by the presence of at least one second polar hard segment having a glass transition temperature or crystalline melting temperature above 37° C., and said second segmented copolymer further characterized by the presence of a polar soft block having a glass transition temperature or crystalline melting temperature below 37° C., said polar hard segments independently selected from the group consisting of a polyurethane and a polyurethaneurea, optionally with the proviso that said base polymer is not a polycarbonate of 4,4'-diphenylmethylmethane, wherein said nonpolar and polar soft blocks control the surface properties of said modified solid polymer blend.

In yet another example, the graft material is a polymer blend for controllably varying the balance of polar to nonpolar groups on the surface of said blend comprising an admixture of a minor portion of a solid thermoplastic polymer additive distributed throughout a major portion of a base polymer, said additive comprising an essentially linear first segmented copolymer chain and a second essentially linear polymer chain chemically bonded to said first segmented copolymer chain, said second polymer chain being selected from a polar homopolymer or a second segmented polymer, said first chain characterized by a $\gamma_c$ less than said base polymer and said first chain segmented copolymer characterized by the presence of at least one polar hard segment having a glass transition temperature or crystalline melting temperature above 37° C., a nonpolar soft block having a glass transition temperature or crystalline melting temperature below 37° C.; said second segmented copolymer or polar homopolymer characterized by the presence of at least one polar hard segment having a glass transition temperature or crystalline melting temperature above 37° C., and said second segmented copolymer further characterized by the presence of a polar soft block having a glass transition temperature of crystalline melting temperature below 37° C., said polar hard segments independently selected from the group consisting of a polyurethane and a polyurethaneurea; with the proviso that said base polymer is not a polycarbonate of 4,4'-diphenyldimethylmethane.

A variety of other biocompatible polyurethanes/polycarbamates and urea linkages (hereinafter "—C(O)N or CON-type polymers") may also be employed. These include CON type polymers that preferably include a soft segment and a hard segment. The segments can be combined as copolymers or as blends. For example, CON type polymers with soft segments such as PTMO, polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

Preferably, the hard segment is formed from a diisocyanate and diamine. The diisocyanate may be represented by the formula OCN—R—NCO, where —R— may be aliphatic, aromatic, cycloaliphatic or a mixture of aliphatic and aromatic moieties. Examples of diisocyanates include MDI, tetramethylene diisocyanate, hexamethylene diisocyanate, trimethyhexamethylene diisocyanate, tetramethylxylylene diisocyanate, 4,4'-dicyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3'-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain oxygen and/or halogen atoms in their structures.

Other applicable biocompatible polyurethanes include those using a polyol as a component of the hard segment.

Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, 1,6-hexanediol, 1,8-octanediol, propylene glycols, 2,3-butylene glycol, dipropylene glycol, dibutylene glycol, glycerol, or mixtures thereof.

Biocompatible CON type polymers modified with cationic, anionic and aliphatic side chains may also be used. See, for example, U.S. Pat. No. 5,017,664. Other biocompatible CON type polymers include: segmented polyurethanes, such as BIOSPAN; polycarbonate urethanes, such as BIONATE; and polyetherurethanes, such as ELASTHANE; (all available from POLYMER TECHNOLOGY GROUP, Berkeley, Calif.). Other biocompatible CON type polymers can include polyurethanes having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Pat. Application Publication No. 2002/0187288 A1, which is incorporated herein by reference.

In addition, any of these biocompatible CON type polymers may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

A graft material polymer may be synthesized by a method of forming a polymer of low surface free energy and increased contact angle hysteresis comprising the steps of (a) reacting up to about 2 volume % of a reactive polysiloxane oligomer with at least 98 volume % of a base polymer, while said oligomer and base polymer are in fluid form to form a fluid polymer admixture of at least 95 volume % pure base polymer and no greater than 5 volume % of a copolymer of said base polymer and said oligomer, and (b) solidifying said polymer ad mixture, said copolymer comprising an essentially linear segmented copolymer chain; said copolymer characterized by a $\gamma_c$ less than said base polymer and said segmented copolymer chain characterized by the presence of at least one polar hard polyurethane or polyurethane urea segment having a glass transition temperature or crystalline melting temperature above 37° C., and a nonpolar polysiloxane soft block having a glass transition temperature or crystalline melting temperature below 37° C., optionally with the proviso that said base polymer is not a polycarbonate of 4,4'-diphenyldimethylmethane and said polymer admixture being characterized by a $\gamma_c$ between about 10 and 35 dyne/cm.

Referring to FIG. 1B, the graft material 30 is preferably formed by one or more layers of a biocompatible polyurethane. The inner portion 36 and/or the outer portion 34 may include one or more layers, of biocompatible polyurethane each having a different composition and/or structure. For example, the graft material 30 may include one or more layers having a therapeutic agent and a non-porous or porous polyetherurethane composition with a siloxane surface modifying additive.

The thickness of the graft material 30 may be selected to provide a desired loading of the therapeutic agent, and desired mechanical properties, such as a suitable durability to the graft material 30 or a desired minimum radius upon radial compression of the stent graft 10 after crimping. The inner portion 36 preferably includes two layers: an inner layer comprising a porous biocompatible polyurethane and the therapeutic agent, and an outer layer including the therapeutic agent and a non-porous biocompatible polyurethane. The inner layer defines the lumen of the medical device 10 and the outer layer contacts the support frame 20. The thickness of the outer layer of the inner portion 36 is typically 1.5-3.0 times thicker than the inner layer of the inner portion 36. The outer portion 34 of the graft material 30 is preferably a multi-layer structure including an inner layer in contact with the support frame 20 and portions of the outer layer of the inner portion 36 through interstitial spaces in the support frame. The inner layer of the outer portion 34 preferably includes a non-porous polyurethane and the therapeutic agent. The outer portion 34 further includes a second layer positioned on the abluminal surface of the inner layer and including a porous polyurethane composition and the therapeutic agent. The inner layer of the outer portion 34 is typically 1.5-3.0 times thicker than the second layer of the outer portion 34. The second layer may form the abluminal surface of the graft material 30, or the outer portion 34 may further include a third layer formed from a non-porous polyurethane material without a therapeutic agent. The third layer of the outer portion 34 preferably forms the abluminal surface of the graft material 30, and is preferably about 1 to 3 times the thickness of the second layer of the outer portion 34.

4. Therapeutic Agents

Preferably, the graft material 30 is formed from one or more layers of non-porous biocompatible polyurethane material mixed with a therapeutically effective amount of a taxane therapeutic agent. A taxane therapeutic composition includes paclitaxel (a compound of the chemical structure shown as structure (1) below) and derivatives thereof. Taxanes in general, and paclitaxel is particular, are taxane therapeutic compounds may function as a cell cycle inhibitor by acting as an anti-microtubule agent, and more specifically as a stabilizer. Preferred taxane therapeutic agents include the core structure with four fused rings ("core taxane structure," shaded in structure (1)), with any therapeutically effective substituents.

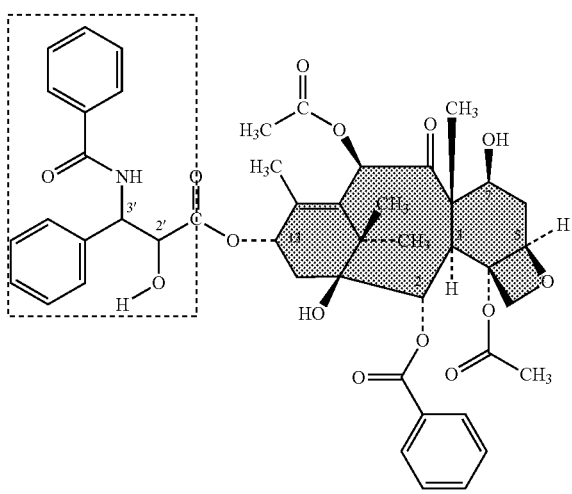

(1)

Paclitaxel has a molecular weight of about 853 amu, and may be readily prepared utilizing techniques known to those skilled in the art (see, e.g., Schiff et al., Nature 277: 665-667, 1979; Long and Fairchild, Cancer Research 54: 4355-4361, 1994; Ringel and Horwitz, J. Nat'l Cancer Inst. 83 (4): 288-291, 1991; Pazdur et al., Cancer Treat. Rev. 19 (4): 351-386, 1993; Tetrahedron Letters 35 (52): 9709-9712, 1994; J. Med. Chem. 35: 4230-4237, 1992; J. Med. Chem. 34: 992-998, 1991; J. Natural Prod. 57 (10); 1404-1410, 1994; J. Natural Prod. 57 (11): 1580-1583, 1994; J. Am. Chem. Soc. 110: 6558-6560, 1988), or obtained from a variety of commercial sources, including for example, Sigma Chemical Co., St. Louis, Mo. (T7402—from *Taxus brevifolia*).

Preferred taxane analogs and derivatives vary the substituents attached to the core taxane structure. In one embodiment, the therapeutic agent is a taxane analog or derivative including the core taxane structure (1) and the methyl 3-(benzamido)-2-hydroxy-3-phenylpropanoate moiety (shown in structure (2) below) at the 13-carbon position ("C13") of the core taxane structure (outlined with a dashed line in structure (1)).

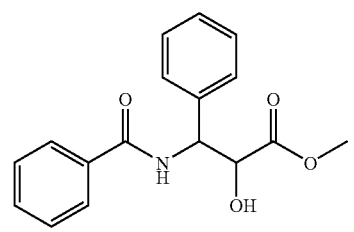

(2)

methyl 3-(benzamido)-2-hydroxy-3-phenylpropanoate

Compounds comprising structure (2) at the 13-carbon position of the core taxane structure may function to alter the biological activity of the taxane molecule as a cell cycle inhibitor. Examples of therapeutic agents having structure (2) include paclitaxel (Merck Index entry 7117), docetaxol (TAXOTERE, Merck Index entry 3458), and 3'-desphenyl-3'-(4-ntirophenyl)-N-debenzoyl-N-(t-butoxycarbonyl)-10-deacetyltaxol.

The rate of release of the therapeutic agent from the stent graft in an elution medium may be recorded as an elution profile of the stent graft. Preferred graft structures are paclitaxel-eluting multi-layer polyurethane graft compositions. The rate of release of the therapeutic agent may be varied by changing the number and composition of layers in the graft structure. An elution profile can be obtained by any suitable method that allows for measurement of the release of the taxane therapeutic agent in a manner that can be measured with a desired level of accuracy and precision. The rate of release of the taxane therapeutic agent can be measured by placing the stent graft in an elution medium and measuring the concentration of the therapeutic agent in the elution medium as a function of time. The elution rate may vary based on both the elution medium being used and the coating configuration.

Figure 2C:
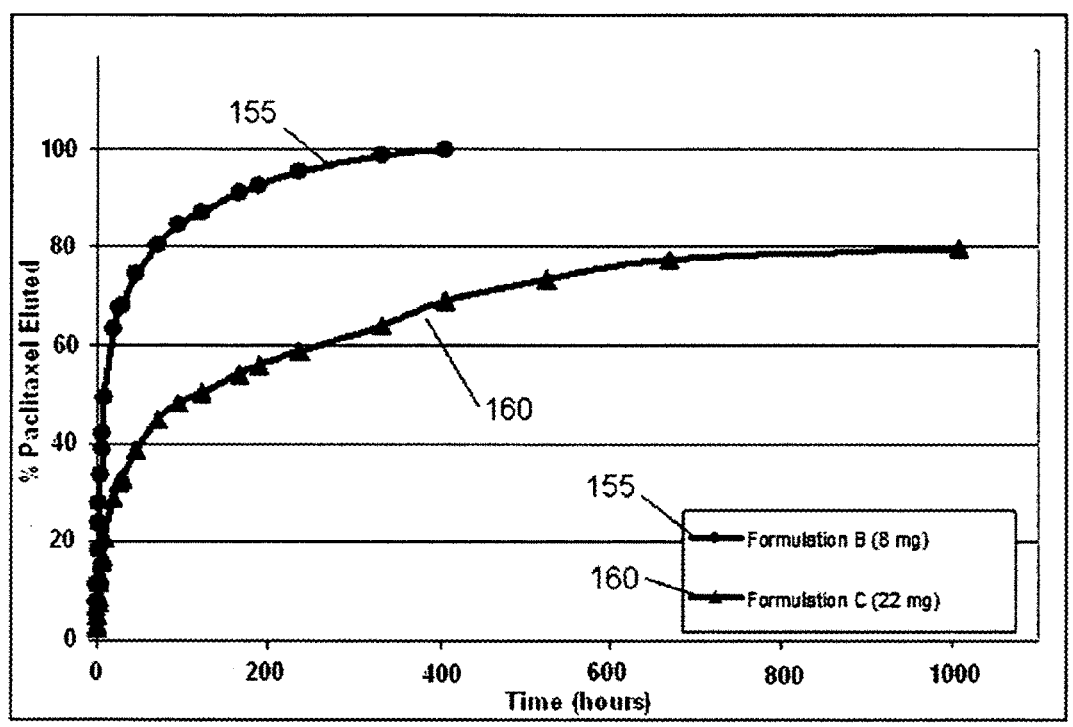
FIG. 2C shows the elution of paclitaxel from two different two-layer stent grafts containing a releasable paclitaxel therapeutic agent at room temperature.

The rate of release of the taxane therapeutic agent can be measured by placing the stent graft in an elution medium and measuring the concentration of the therapeutic agent in the elution medium as a function of time. FIGS. 2A-2C show elution profiles for the release of paclitaxel from different stent graft structures in an elution medium comprising a 0.5% aqueous solution of sodium dodecyl sulfate (SDS). The SDS elution medium dissolves a taxane therapeutic agent more rapidly than a porcine serum elution medium. The elution profiles show the percentage of the taxane therapeutic agent released from the different stent grafts as a function of time the stent graft was in contact with the elution medium. To obtain the elution profiles in FIGS. 2A-2C, the amount of paclitaxel released from each graft was measured measuring an ultraviolet spectrum of the elution medium as a function of time the graft is in contact with the elution medium. The core taxane structure (1) can be identified from an ultraviolet (UV) spectrum of the taxane therapeutic agent in any suitable elution medium that permits measurement of a characteristic peak of the taxane therapeutic agent in solution. Ethanol is another preferred example of a suitable solvent. An ultraviolet (UV) spectrum (Agilent In-line UV Spectrophotometer) of paclitaxel in ethanol shows a characteristic peak at 227 nm indicative of the presence of the core taxane structure in the solution. The characteristic peak at about 227 nm can be correlated to the presence of the taxane therapeutic agent in the elution medium solution.

TABLE 1

| Curve | Total PTX (mg) | Inner portion (36), inner layer (relative thickness) | Inner portion (36), outer layer (relative thickness) | Outer portion (34), inner layer (relative thickness) | Outer portion (34), middle layer (relative thickness) | Outer portion (34), outer layer (relative thickness) |
|---|---|---|---|---|---|---|
| 110 | 60 | Porous + PTX (1) | Non-porous + PTX (3) | Non-porous + PTX (3) | Porous + PTX (1) | Non-porous (3) |
| 120 | 67 | Porous + PTX (2) | Non-porous + PTX (3) | Non-porous + PTX (3) | Porous + PTX (2) | Non-porous (3) |
| 130 | 51 | Porous + PTX (1) | Non-porous + PTX (3) | Non-porous + PTX (3) | Porous + PTX (1) | Non-porous (2) |
| 140 | 50 | Porous + PTX (1) | Non-porous + PTX (3) | Non-porous + PTX (3) | Porous + PTX (1) | Non-porous (1) |
| 150 | 59 | Porous + PTX (2) | Non-porous + PTX (3) | Non-porous + PTX (3) | Porous + PTX (2) | Non-porous (1) |

Referring again to FIG. 1B, Table 1 describes a series of five examples of multi-layer graft materials 30. Table 1 describes the composition and structure of an inner portion 36 including an inner layer and an outer layer, both positioned on the luminal side of the support structure 20. The outer layer of the inner portion 36 contacts the luminal side of the support structure, while the inner layer contacts and defines the lumen 6. The outer portion 34 has a three-layer structure including an inner layer, a middle layer and an outer layer, with compositions described in separate columns in Table 1. The inner layer of the outer portion 34 contacts the support structure 20 and portions of the outer layer of the inner portion 36 through openings in the support structure 20. The outer layer of the outer portion 34 contacts the lubricious polymer coating 32 and the middle layer positioned between the outer layer and the inner layer of the outer portion 34. Each layer includes a biocompatible polyurethane that is porous or non-porous, as indicated in Table 1. The relative thicknesses of each layer to one another, and the total amount of paclitaxel ("PTX") in the entire tubular graft material 30 are also indicated in Table 1. Layers containing paclitaxel are also designated as "PTX" in the corresponding layer.

The rate of paclitaxel elution obtained by contacting each of the five tubular graft materials 30 in Table 1 in 0.5% sodium dodecyl sulfate (SDS) aqueous solution in an in vitro elution test medium. FIG. 2A shows the elution profiles obtained from these five different multi-layer paclitaxel-eluting stent grafts 30 having the layer compositions indicated in Table 1. The stent graft corresponding to curve 110 had a thickness ratio of 1:3/3:1:3, where the "/" indicates the position of the support frame and the numbers represent the thickness of the layers with respect to each other from the luminal surface (left) to the abluminal surface (right). Curves 120, 130, 140 and 150 having different thickness ratios, as indicated in Table 1, were also measured for different stent grafts in separate samples of the same elution medium. The graft material measured to obtain curve 120 was different from the graft for curve 110 except in that (1) the thickness of the inner layer of the porous THORALON inner portion and the middle layer of the outer portion were each twice as thick as the corresponding layers in the graft for curve 110 and (2) the amount of paclitaxel was different. The grafts measured to obtain curves 130 and 140 were different in that (1) the graft for curve 110 except that the thickness of the outer layers of the non-porous THORALON outer portions were thinner than the corresponding layers in the graft for curve 110 and (2) the amount of paclitaxel was different. The graft measured to obtain curve 150 differed from the graft for curve 120 in that (1) the thickness of the outer layer of the non-porous THORALON outer portion was thinner than the corresponding layers in the graft for curve 120 and (2) the paclitaxel content was lower. The total thickness of each of the multi-layer grafts was about 0.10 mm. Each graft material was formed using a 200 mM paclitaxel concentration in the polyurethane FIG. 2B shows the comparative elution rates of paclitaxel from a series of stent grafts configured according to structures "A," "B," and "C" described in Table 10 in Example 3 below. The elution rates were measured at room temperature (25° C.) in an elution medium comprising a 0.5% aqueous solution of sodium dodecyl sulfate (SDS) as described above with respect to the elution rates shown in FIG. 2A. The total amount of paclitaxel in the stent grafts ranged from 11 mg in the stent grafts for curves 122 (structure B) and 132 (structure A), to 17 mg for curves 142 and 152 (structure A), to a maximum of 26 mg for the stent graft used to obtain curve 112 (structure C). Notably, curve 112 was the slowest-eluting and was obtained from the stent graft with the stent graft with the highest amount of paclitaxel among the stent grafts tested to obtain the data shown in FIG. 2B. Unexpectedly, the curves 112, 122, 132, 142 and 152 shown in FIG. 2B all indicate a more rapid elution rate obtained from stent grafts with lower total amounts of paclitaxel than the stent grafts used to obtain elution curves 110, 120, 130, 140 and 150 in FIG. 2A. Surprisingly, stent grafts with higher loadings (51 mg-67 mg) of paclitaxel (shown in FIG. 2A) showed a slower elution rate in the same elution medium at room temperature than the stent grafts with lower loadings (11 mg-17 mg) tested to obtain the data shown in FIG. 2B.

Figure 2D:
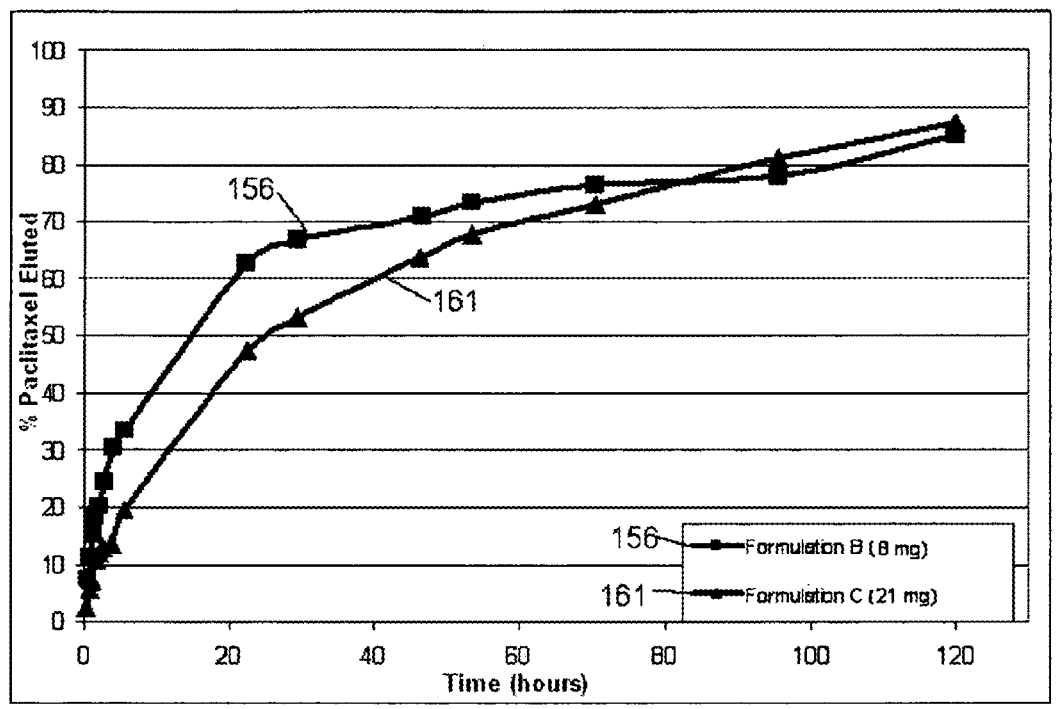
FIG. 2D shows the elution of paclitaxel from two different two-layer stent grafts containing a releasable paclitaxel therapeutic agent at 37° C.

FIG. 2C shows elution profiles obtained from two different two-layer paclitaxel-eluting stent grafts having the four layer structure and composition indicated in Table 2 below. Both elution profiles were measured at room temperature (25° C.) in a 0.5% aqueous solution of sodium dodecyl sulfate (SDS). The total thickness of each graft material was about 0.10 mm. The graft of curve 155 and the graft of curve 160 differed only in the total amount of paclitaxel loaded in the graft. Surprisingly, the higher loading in the graft of curve 160 resulted in slower and a more sustained release than the graft of curve 155. Increasing the amount of paclitaxel in the graft decreased the elution rate. Each layer containing paclitaxel may be formed by any suitable method, such as spray coating a solution comprising about 200 mM paclitaxel in a volatile solvent, such as dimethylene chloride, and the THORALON polymer components described above. Elution profiles were measured at 37° C. for additional comparable paclitaxel-eluting stent grafts with the composition indicated in Table 2, resulting in the elution profiles shown in FIG. 2D. Unexpectedly, the rate of elution for the stent graft having the lower total amount of paclitaxel (8 mg) indicated by curve 156 was slower at 37° C. in FIG. 2D than the rate of elution shown by curve 155 measured at 25° C. in FIG. 2C. Similarly, the rate of elution measured for the stent graft with the higher total amount of paclitaxel (22 mg total) indicated by curve 161 was slower at 37° C. than the curve 160 measured at 25° C. in FIG. 2C. The rate of elution measured at 37° C., as shown in FIG. 2D, remained faster for the stent graft having a lower total amount of paclitaxel (curve 156) than for the stent graft having a higher total amount of paclitaxel (curve 161).

TABLE 2

| Curves | Total PTX (mg) | Inner portion, inner layer (relative thickness) | Inner portion, outer layer (relative thickness) | Outer portion, inner layer (relative thickness) | Outer portion, outer layer (relative thickness) |
|---|---|---|---|---|---|
| 155 156 | 8 | Porous + PTX (1) | Non-porous + PTX (5) | Non-porous + PTX (5) | Non-porous + PTX (2) |
| 160 161 | 22 | Porous + PTX (1) | Non-porous + PTX (5) | Non-porous + PTX (5) | Non-porous + PTX (2) |

Figure 2E:
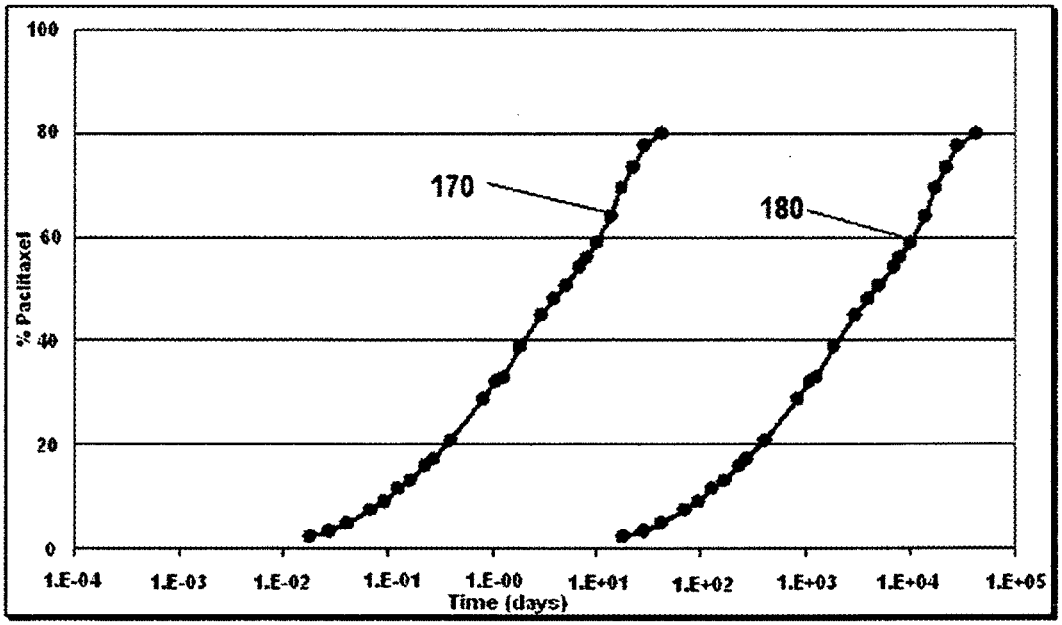
FIG. 2E shows the elution of paclitaxel from a two-layer stent graft containing a releasable paclitaxel therapeutic agent in an elution medium of 0.5% aqueous solution of SDS and an estimated elution profile for the two-layer paclitaxel-releasing stent graft in a porcine serum elution medium.

FIG. 2E shows an elution profile 170 obtained for a single two-layer paclitaxel-eluting stent graft having the layer compositions indicated in Table 3 below, measured in the 0.5% aqueous SDS solution used as an elution medium for data in FIGS. 2A and 2B, and a projected elution profile 180 for the same stent graft in a porcine serum elution medium. The outer layer of the inner portion and the inner layer of the outer portion form a single continuous layer through the openings in the support frame, and separate layers on either side of the support frame struts. Paclitaxel elutes more slowly in porcine serum than in the SDS solution. The projected elution medium 180 was calculated based on the ratio of the solubility of paclitaxel in SDS and porcine serum. The total thickness of each graft material was about 0.10 mm.

The graft configurations corresponding to the elution profiles in FIGS. 2A-2C may further include a lubricious polymer coating material deposited on the abluminal surface of the graft. Referring again to FIG. 1B, a lubricious polymer coating 32 is preferably readily soluble in the elution medium, or within the body, to provide for ease of crimping and delivery without changing the elution profile. Typically, the lubricious polymer coating is rapidly dissolved upon delivery of the stent graft within the body vessel (e.g., minutes to hours), much more rapidly than the rate of elution of the therapeutic agent (e.g., weeks to months).

TABLE 3

| Curve | Total PTX (mg) | Inner portion, inner layer (relative thickness) | Inner portion, outer layer (relative thickness) | Outer portion, inner layer (relative thickness) | Outer portion, outer layer (relative thickness) |
|---|---|---|---|---|---|
| 170, 180 | 17 | Porous + PTX (1) | Non-porous + PTX (5) | Non-porous + PTX (5) | Non-porous + PTX (2) |

Another preferred graft configuration is a four layer polyurethane paclitaxel-eluting coating summarized in Table 4, having an inner portion 36 with an inner layer of non-porous polyurethane and an outer layer of non-porous polyurethane and paclitaxel in contact with the luminal surface of the support frame, an outer portion 34 having an inner layer formed from paclitaxel and non-porous polyurethane and an outer layer formed from non-porous polyurethane, and a lubricious outer polymer coating 32 of polyethylene glycol (PEG). The relative thicknesses of the layers are shown in Table 4. The total thickness is about 0.07 mm. The outer layer of the inner portion and the inner layer of the outer portion form a single continuous layer through the openings in the support frame, and separate layers on either sides of the support frame struts. The polyurethane is preferably non-porous THORALON, and the paclitaxel is preferably evenly distributed in the outer layer of the inner portion and the inner layer of the outer portion.

TABLE 4

| Total PTX (mg) | Inner portion, inner layer (relative thickness) | Inner portion, outer layer (relative thickness) | Outer portion, inner layer (relative thickness) | Outer portion, outer layer (relative thickness) | Total PEG (mg) |
|---|---|---|---|---|---|
| 15 | Non-porous (1) | Non-porous + PTX (1) | Non-porous + PTX (2) | Non-porous (1) | 14 |

Another preferred graft configuration is a two-layer polyurethane paclitaxel-eluting coating summarized in Table 5. The stent graft includes two layers, and a lubricious polymer coating of PEG applied to the abluminal surface of the graft. The total thickness is about 0.07 mm, not including the PEG coating. The polyurethane is preferably non-porous THORALON, and the paclitaxel is preferably evenly distributed in the inner portion and the outer portion.

TABLE 5

| Total PTX (mg) | Inner portion (relative thickness) | Outer portion, inner layer (relative thickness) | Total PEG (mg) |
|---|---|---|---|
| 15 | Non-porous + PTX (1) | Non-porous + PTX (1) | 10 |

Optionally, the graft material 30 may further include an antithrombogenic bioactive agent. An antithrombogenic bioactive agent is any therapeutic agent that inhibits or prevents thrombus formation within a body vessel. The medical device can comprise any suitable antithrombogenic bioactive agent. Types of antithrombotic bioactive agents include anticoagulants, antiplatelets, and fibrinolytics. Anticoagulants are bioactive agents which act on any of the factors, cofactors, activated factors, or activated cofactors in the biochemical cascade and inhibit the synthesis of fibrin. Antiplatelet bioactive agents inhibit the adhesion, activation, and aggregation of platelets, which are key components of thrombi and play an important role in thrombosis. Fibrinolytic bioactive agents enhance the fibrinolytic cascade or otherwise aid is dissolution of a thrombus. Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin. Further examples of antithrombotic bioactive agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

5. Lubricious Polymer Coatings

The abluminal surface of the graft material 30 may be coated with a lubricious polymer coating 32 configured to reduce the frictional forces incident on the graft material 30 during radial compression of the stent graft 10. Preferably the lubricious polymer coating 32 is a removable material that is readily dissolved within the body vessel as the stent graft 10 is being deployed from a catheter delivery system. The removable material of the lubricious polymer coating 32 is desirably durable, solid, and flexible at room temperature, and dissolves readily when exposed to blood under normal blood temperatures and pH. The rate of dissolution of the removable materials can be varied by changing the molecular weights of the removable material. Typically, the lower the molecular weight of a removable material polymer, the faster the removable material will dissolve. The molecular weight of the polymer can be selected to provide a desired rate of dissolution and durability. Some polymers, such as chondroitin sulfate, may occur in nature with a molecular weight as high as 25,000, while others, such as hydroxypropylmethyl cellulose might be as high as 1,000,000. Hyaluronate may have a molecular weight as great as 8,000,000. Preferably, the removable material is a water-soluble polymer that it rapidly imbibes water and softens and/or dissolves within an aqueous substance. The molecular weight of the polymer should be high enough so that the wet polymer has enough strength and film integrity remain intact during delivery of the medical device through a body vessel, and low enough so that the removable material will dissolve rapidly during deployment of the medical device. Varying the thickness or adding perforations will also increase the rate of dissolution of the removable material materials.

Preferably, the lubricious polymer coating 32 consists essentially of a polymer comprising polyethylene or polyacrylic acid. For example, the lubricious polymer material is most preferably a polyethyleneoxide or glycol, preferably biocompatible glycols, including polyglycols, such as polyethylene glycol (PEG), propylene glycol, glycerin, polyglycol co-polymers and polyols that form coatings that are smooth and lubricious. A glycol lubricious polymer such as poly(ethylene glycol) (PEG) may have a weight average molecular weight in the range from 100 to about 10,000 (preferably 1,000). The removable material may also include the removable material comprises one or more esters of poly(meth)acrylic acid wherein the ester group may be represented by the formula—OR in which the R moiety is sufficiently small (e.g., methyl or ethyl or other C1 or C2 type of moiety) so that the polymer is water soluble; similar esters of polyvinyl alcohol; combinations of these, and the like. Most preferably, the water soluble material is PEG, more preferably PEG having a weight average molecular weight of about 8000. Hyaluronate may also be used as a removable material.

The amount of the lubricious polymer in the coating 32 may be selected based on the amount of therapeutic agent, so as to provide a stent graft characterized by a desired release rate of the therapeutic agent. The total amount of a lubricious polymer such as PEG applied to the abluminal surface of the graft material is preferably provided in an amount that permits crimping of the coated stent graft comprising a releasable therapeutic agent to a desired radially compressed diameter and loading into a delivery device. In addition, the amount of the lubricious polymer is preferably selected to permit the stent graft to be expanded from the radially compressed configuration within a body vessel and to subsequently release a therapeutic agent from the abluminal surface of the stent graft at a desired rate. Preferably, the amount of lubricious polymer is selected so as to provide adequate protection against physical damage to the graft material during crimping and expansion of the stent graft, without undesirably altering the rate of release of the therapeutic agent within a body vessel at an intended point of treatment.

For example, for a stent graft comprising a releasable paclitaxel therapeutic agent and a PEG lubricious polymer, the weight ratio of the therapeutic agent and the PEG polymer is preferably between about 0.10 and 3.50, and most preferably between about 0.10 and 1.50. Table 6 describes four particularly preferred stent grafts for delivering paclitaxel to a body vessel. The stent grafts may have a radially expandable frame having a diameter of about 10 mm in the radially expanded configuration and a stent graft material attached to the frame. The stent graft material may be a biocompatible polyurethane including a releasable therapeutic agent such as paclitaxel. For example, the graft may be configured to release therapeutically effective amount (e.g., 10-15 mg) of paclitaxel over a period of weeks or months, preferably with O-order kinetics. The amount of PEG applied to the abluminal surface of the graft is most preferably selected to provide a paclitaxel:PEG weight ratio of about 0.10-3.50, and most preferably about 0.10-1.50. Stent grafts having preferred weight ratios of paclitaxel:PEG may provide desired elution rates of the therapeutic agent, and be resistant to physical damage during radial compression and expansion typically encountered during the crimping and delivery process employed in intraluminal delivery with a catheter-based delivery system.

TABLE 6

| Frame Expanded Outer Diameter (mm) | Frame Length (mm) | Stent Graft Abluminal Surface Area (mm²) | Total Paclitaxel in Stent Graft (mg) | Total PEG Coated on Abluminal Surface of Stent Graft (mg) | Dose of Paclitaxel in Stent Graft (micrograms/ mm²) | Dose of PEG in Stent Graft Coating (micrograms/ mm²) | Weight Ratio of Paclitaxel in Stent Graft to PEG Coating (mg:mg) |
|---|---|---|---|---|---|---|---|
| 10 | 90 | 2826 | 10 | 100 | 3.54 | 35.39 | 0.10 |
| 10 | 90 | 2826 | 15 | 100 | 5.31 | 35.39 | 0.15 |
| 10 | 90 | 2826 | 10 | 10 | 3.54 | 3.54 | 1.00 |
| 10 | 90 | 2826 | 15 | 10 | 5.31 | 3.54 | 1.50 |

In other examples, the stent graft may have about 10-100 micrograms of PEG/mm² of abluminal surface area of the stent graft and at about 3-20) micrograms/mm² of the therapeutic agent within the graft. For example, a stent graft having a radially expanded diameter of about 6 mm and a length of about 40 mm may include about 2-20 mg (about 3-27 μg/mm²) of PEG coated on the abluminal surface of the graft, with about 3-20 mg of paclitaxel incorporated within the graft material and releasable through the abluminal surface of the stent graft.

6. Support Frames

The stent graft preferably includes a means for supporting the graft material in a desired configuration, such as the support frame 20. Preferably, the support means includes a radially expandable support frame, such as a self-expanding support frame. The support frame 20 can be formed from any suitable structure that maintains an attached graft material in a desired position, orientation or range of motion to perform a desired function. Preferably, the support frame 20 is a radially self-expandable support frame adapted for implantation within a body vessel from a delivery catheter. In another aspect, the support means can include a sinusoidal hoop member.

The support frame 20 preferably defines a substantially cylindrical or elliptical lumen providing a conduit for fluid flow. The frame structure may comprise a plurality of struts, which can be of any suitable structure or orientation. In some embodiments, the frame comprises a plurality of struts connected by alternating bends. For example, the frame can be a ring or annular tube member comprising a series of struts in a "zig-zag" pattern. The frame can also comprise multiple ring members with struts in a "zig-zag" pattern, for example by connecting the ring members end to end, or in an overlapping fashion. In some embodiments, the struts are substantially aligned along the surface of a tubular plane, and substantially parallel to the longitudinal axis of the support frame. Support frames can also be formed from braided strands of one or more materials, helically wound strands, ring members, consecutively attached ring members, tube members, and frames cut from solid tubes. The support frame is preferably selected for an intended site of implantation, such as placement to treat a biliary tract tumor. For example, a ZILVER intravascular stent (Cook Inc., Bloomington, Ind.) may be used. In one example, the frame has a diameter in a radially expanded configuration of about 9-10 mm and a length of about 40 mm-80 mm. A suitable graft material, such as a biocompatible polyurethane, is preferably adhered to the luminal and abluminal surfaces of the frame.

The specific implantable frame chosen will depend on several considerations, including the size and configuration of the vessel and the size and nature of the medical device. The frame can perform any desired function, including a stenting function. The frame configuration may be selected based on several factors, including the vessel in which the medical device is being implanted, the axial length of the treatment site, the inner diameter of the body vessel, and the desired delivery method for placing the support structure. Those skilled in the art can determine an appropriate stent based on these and other factors. The implantable frame can be sized so that the expanded configuration is slightly larger in diameter that the inner diameter of the vessel in which the medical device will be implanted. This sizing can facilitate anchoring of the medical device within the body vessel and maintenance of the medical device at a point of treatment following implantation. Preferably, the support frame has an expanded inner diameter of about 5 mm to about 25 mm, more preferably about 4 mm to about 8 mm and most preferably about 6 mm. The support frame can have any suitable length. The length of the support frame is selected based on the desired site of implantation. Examples of suitable frame lengths include frames with a length of about 10 to 100 mm long, more preferably about 20-80 mm and most preferably about 40-80 mm for biliary applications.

The implantable frame may be formed from any suitable biocompatible material that allows for desired therapeutic effects upon implantation in a body vessel. Examples of suitable materials include, without limitation, any suitable metal or metal alloy, such as: stainless steels (e.g., 316, 316L or 304), nickel-titanium alloys including shape memory or superelastic types (e.g., nitinol or elastinite); inconel; noble metals including copper, silver, gold, platinum, palladium and iridium; refractory metals including molybdenum, tungsten, tantalum, titanium, rhenium, or niobium; stainless steels alloyed with noble and/or refractory metals; magnesium; amorphous metals; plastically deformable metals (e.g., tantalum); nickel-based alloys (e.g., including platinum, gold and/or tantalum alloys); iron-based alloys (e.g., including platinum, gold and/or tantalum alloys); cobalt-based alloys (e.g., including platinum, gold and/or tantalum alloys); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; platinum-iridium alloys; platinum-tungsten alloys; magnesium alloys; titanium alloys (e.g., TiC, TiN); tantalum alloys (e.g., TaC, TaN); L605; bioabsorbable materials, including magnesium; or other biocompatible metals and/or alloys thereof.

In some embodiments, the implantable frames impart radially outward directed force during deployment, whether self-expanding or radially-expandable. The radially outward directed force can serve to hold the body lumen open against a force directed radially inward, as well as preventing restriction of the passageway through the lumen by intimal flaps or dissections generated by, such as prior balloon angioplasty. Another function of the radially outward directed force can also fix the position of the stent within the body lumen by intimate contact between the stent and the walls of the lumen. Preferably, the outwardly directed forces do not traumatize the lumen walls. Preferably, the frame material is capable of significant recoverable strain to assume a low profile for delivery to a desired location within a body lumen. After release of the compressed self-expanding resilient material, it is preferred that the frame be capable of radially expanding back to its original diameter or close to its original diameter. Accordingly, some embodiments provide frames made from material with a low yield stress (to make the frame deformable at manageable balloon pressures), high elastic modulus (for minimal recoil), and is work hardened through expansion for high strength. Particularly preferred materials for self-expanding implantable frames are shape memory alloys that exhibit superelastic behavior, i.e., are capable of significant distortion without plastic deformation. Frames manufactured of such materials may be significantly compressed without permanent plastic deformation, i.e., they are compressed such that the maximum strain level in the resilient material is below the recoverable strain limit of the material. Other embodiments provide frames that are not self-expanding, or that do not comprise superelastic materials. Preferably, the implantable frame comprises a self-expanding nickel titanium (NiTi) alloy material, stainless steel or a cobalt-chromium alloy.

Preferably, the support frame 20 is self-expanding. Upon compression, self-expanding frames can expand toward their pre-compression geometry. In some embodiments, a self-expanding frame can be compressed into a low-profile delivery conformation and then constrained within a delivery system for delivery to a point of treatment in the lumen of a body vessel. At the point of treatment, the self-expanding frame can be released and allowed to subsequently expand to another configuration. Discussions relating to nickel titanium alloys and other alloys that exhibit behaviors suitable for frames can be found in, e.g., U.S. Pat. No. 5,597,378 (Jervis) and WO 95/31945 (Burmeister et al.). A preferred shape memory alloy is Ni—Ti, although any of the other known shape memory alloys may be used as well. Such other alloys include: Au—Cd, Cu—Zn, In—Ti, Cu—Zn—Al, Ti—Nb, Au—Cu—Zn, Cu—Zn—Sn, CuZn—Si, Cu—Al—Ni, Ag—Cd, Cu—Sn, Cu—Zn—Ga, Ni—Al, Fe—Pt, U—Nb, Ti—Pd—Ni, Fe—Mn—Si, and the like. These alloys may also be doped with small amounts of other elements for various property modifications as may be desired and as is known in the art, Nickel titanium alloys suitable for use in manufacturing implantable frames can be obtained from, e.g., Memory Corp., Brookfield, Conn. One suitable material possessing desirable characteristics for self-expansion is Nitinol, a Nickel-Titanium alloy that can recover elastic deformations of up to 10 percent. This unusually large elastic range is commonly known as superelasticity.

Suitable implantable frames can also have a variety of configurations, including braided strands, helically wound strands, ring members, consecutively attached ring members, tube members, and frames cut from solid tubes. Also, suitable frames can have a variety of sizes. The exact configuration and size chosen will depend on several factors, including the desired delivery technique, the nature of the vessel in which the device will be implanted, and the size of the vessel. A frame structure and configuration can be chosen to facilitate maintenance of the device in the vessel following implantation. The implantable frame can be formed in any suitable shape, including a ring, a stent, a tube, or a zig-zag configuration. In one embodiment, the implantable frame can be self-expanding or balloon-expandable.

7. Methods of Manufacture

In a second embodiment, methods for making a stent graft for placement within a body passage are also provided. Preferably, the prosthetic valve comprises a releasable therapeutic agent. According to one preferred method, the stent graft is formed by spraying a solution comprising a dissolved thromboresistant material and a therapeutic agent is applied to a mandrel and dried to form a series of layers.

The graft is preferably formed from a biocompatible polyurethane material, such as THORALON, can be attached to an implantable support frame by drying a solution of the dissolved thromboresistant material onto the luminal and abluminal surfaces of the support frame. The dried polyurethane material can adhere to the support frame, or two layers of the dried polyurethane material on either side of the support frame can be attached to each other through interstitial holes in the support frame.

The thromboresistant polyurethane material can be formed by at least one of three methods: (1) spraying, (2) dipping or (3) casting of the biocompatible polyurethane solution, and drying the polymer around portions of a support frame. Alternatively, a dried sheet of biocompatible polyurethane material can be adhered to a support frame using an adhesive, sutures, UV-activated polymers, melting, or any suitable means of attachment providing a desirably durable attachment between the thromboresistant material and the implantable frame. Preferably, a solution of the dissolved thromboresistant material can be coated onto a portion of the frame and attached to the frame as the solution is dried.

7a. Polyurethane Solution Preparation

A graft material comprising the graft polymer and the therapeutic agent can be formed by spray coating a solution comprising a dissolved thromboresistant material in a volatile organic solvent by spraying, dipping or casting. The solution can be dried by removal of the organic solvent to form a portion of an implantable valve. The solution is preferably a polyurethane dissolved in a suitable solvent.

For graft layers comprising the therapeutic agent, the therapeutic agent is preferably incorporated into the solution with the polyurethane and organic solvent. The concentration of the therapeutic agent in the solution is preferably about 10-500 mM, more preferably about 50-300 mM and most preferably about 200 mM in the organic solvent. Most preferably, the solution is a 200 mM solution of paclitaxel in dimethylacetamide (DMAC) with the polyurethane.

A solution for forming non-porous biocompatible polyurethane (e.g., THORALON) can be made by mixing the polyetherurethane urea (BPS-215) and the surface modifying additive (SMA-300) in a solvent, such as dimethyl formamide (DMF), tetrahydrofuran (THF), dimethyacetamide (DMAC), or dimethyl sulfoxide (DMSO). The solution typically contains between about 1% and 5% by weight SMA-3000 for either spray or dip coating solutions. The composition can contain up to about 40 wt % BPS-215 polymer, and different levels of polymer within the range can be used to fine tune the viscosity needed for a given process. Preferably, a solution for spray coating contains less than about 25% by weight of BPS-215 and SMA-3000 in a DMAC solvent, with a viscosity of less than about 2,000 Cp. Typical spray solutions can include a 50:50 weight percentage blend of the DMAC solvent and the pre-mixed solid composition comprising the BPS-215 and SAM-300. Solutions for dip coating can contain more BPS-215, having a viscosity of between about 2,000 and 3,000 Cp. The composition can contain less than 5 wt % polymer for some spray application embodiments. The entire composition can be cast as a sheet, or coated onto an article such as a mandrel or a mold.

A solution for forming porous THORALON can be made by mixing the polyetherurethane urea (BPS-215), the surface modifying additive (SMA-300) and micronized water soluble salt in a solvent a suitable solvent described above, preferably DMAC. The salt is preferably sodium chloride sieved at up to about 20-70 µm particle size. The amount of salt can be increased to increase the porosity of the polyurethane produced. Preferably, the weight of salt added to the solvent is about 5-15 times the amount of solid BPS-215 and SMA-300 added to the solvent, more preferably about 6-12 times. The solution typically contains between up to about 1% to 5% by weight SMA-3000 for either spray or dip coating solutions. The composition can contain up to about 40 wt % BPS-215 polymer, and different levels of polymer within the range can be used to fine tune the viscosity needed for a given process. Preferably, a solution for spray coating contains less than about 25% by weight of BPS-215 and SMA-3000 in a DMAC solvent, with a viscosity of less than about 2,000 Cp. Typical spray solutions can include a 50:50 weight percentage blend of the DMAC solvent and the pre-mixed solid composition comprising the BPS-215 and SAM-300. Solutions for dip coating can contain more BPS-215, having a viscosity of between about 2,000 and 3,000 Cp. The composition can contain less than 5 wt % polymer for some spray application embodiments. The entire composition can be cast as a sheet, or coated onto an article such as a mandrel or a mold.

7b. Mandrel-Frame Spray Coating

In a first aspect, a stent graft is formed by spray coating the solution described above (including a polyurethane in a suitable solvent) onto a cylindrical mandrel. The mandrel can be made from any suitable material that permits the thromboresistant material to be coated, dried on and removed from the mandrel surface. Suitable materials include stainless steel and glass.

To form a stent graft, the mandrel surface is sprayed with the polyurethane solution, optionally including the therapeutic agent, and the solvent is evaporated. The polyurethane solution may be applied in multiple passes to provide a desired thickness. For example, a non-porous THORALON solution may be applied to a mandrel to form the inner layer of an inner portion of a graft material. After drying the coating, a second solution comprising a porous or non-porous THORALON solution and a desired amount of a therapeutic agent may be applied to the inner layer on the mandrel to form an outer layer of the inner portion of the graft materials. A cylindrical self-expanded support frame may be placed over the dried inner portion and one or more layers of an outer portion of the graft coating may be sequentially applied over the support frame and inner portion of the graft material. After applying and drying one or more layers of a porous or non-porous THORALON solution with or without the therapeutic agent, the entire stent graft structure may be removed from the mandrel.

The solution can also be applied to the mandrel and/or frame by dipping a mandrel, an implantable frame, or an assembly comprising both the mandrel and the implantable frame in the solution of dissolved thromboresistant material.

7c. Casting

A tubular sleeve of THORALON polyurethane material can alternatively be attached to a series of coaxially-aligned hoop members by casting. One or more sinusoidal ring members formed from a self-expanding biocompatible metal or metal alloy can be placed inside the tubular mold, typically a glass or quartz tube having an inner diameter equal to the desired outer diameter of the stent graft. Preferably, a first layer of polyurethane coating is first applied to the interior surface of the mold by placing a small amount of the polyurethane solution preparation into the mold, and heating the mold while rotating the mold to evaporate the solvent from the solution, leaving a thin coating of the polyurethane on the interior surface of the mold. Then, one or more ring members, or any suitable frame (such as a stent), is placed inside the coated mold. The ring members can be positioned at either end of the mold. Next, additional coating layers of the polyurethane material can be deposited over the sinusoidal members by adding more of the solution inside the mold, and heating the solution to evaporate the solvent with adequate ventilation. The additional layers can join to the first layer to form a continuous outer sleeve that surrounds the sinusoidal ring members in a "sandwich" manner. The sinusoidal ring members can be formed from a self-expanding material having an expanded state with a wider diameter than the interior diameter of the tubular mold, so as to exert a force in an outward radial direction after formation of the polyurethane coating to the device.

The polyurethane can be coated on the interior surface of the tubular mold by drying a polyurethane solution inside a suitable tubular mold (such as a quartz tube) while rotating the tubular mold to provide an outer sleeve structure. First, a suitable polyurethane solution, such as porous or non-porous THORALON, is prepared. The solution preferably has a weight ratio of solid (BPS-215 and SMA-300, and optionally containing a salt for forming the porous THORALON material) to DMAC of between about 1:1.5 to about 2:1. The solution can be coated on the inner surface of a glass tubular mold. The coated glass tube can be rotated at about 5 rpm along its longitudinal axis while being heated at a temperature and for a time sufficient to evaporate the solvent (e.g., about 40° C. for about 2 hours). Optionally, hoop members or reinforcing elements (e.g., carbon fibers) can then be placed in contact with the dried coating inside the tube. Another layer of the solution can then be applied to the inside surface of the tube containing the hoop members or reinforcing elements. The glass tube is again heated and rotated to evaporate the solvent, leaving a casted structure having a tubular configuration and incorporating the hoop members or reinforcing elements within the polyurethane wall of the structure. The dried sleeve structure containing the hoop members can be removed from the glass tube and soaked in a warm water bath at a temperature of about 65° C. for about 1 hour, then removed and dried. Optionally, a valve can be radially compressed, deployed and then secured within the lumen of the outer sleeve. The diameter of the tubular mold is preferably less than the maximum diameter of the fully expanded hoop member of valve. Preferably, the valve and hoop members are self-expanding structures that provide an outward radial force to provide shape and stability to the outer sleeve.

7d. Applying Lubricious Polymer Coating

Preferably, polyethylene glycol (PEG) or other lubricious soluble coating is applied to the abluminal surface of the stent graft using ultrasonic coating, to provide a smooth and uniform polymer coating. Preferably, the PEG polymer coating is applied from an ultrasonic nozzle. A solution of 8 g/L PEG in a suitable solvent such as dichloromethane can be applied using an ultrasonic nozzle. Ultrasonic nozzles can be configured such that excitation of the piezoelectric crystals creates a transverse standing wave along the length of the nozzle. The ultrasonic energy originating from the crystals located in the large diameter of the nozzle body undergoes a step transition and amplification as the standing wave as it traverses the length of the nozzle. The ultrasonic nozzle can be designed so that a nodal plane is located between the crystals. For ultrasonic energy to be effective for atomization, the atomizing surface (nozzle tip) is preferably located at an anti-node, where the vibration amplitude is greatest. To accomplish this, the nozzle's length must be a multiple of a half-wavelength. Since wavelength is dependent upon operating frequency, nozzle dimensions can be related to operational frequency. In general, high frequency nozzles are smaller, create smaller drops, and consequently have smaller maximum flow capacity than nozzles that operate at lower frequencies. The ultrasonic nozzle can be operated at any suitable frequency, including 24 kHz, 35 kHz, 48 kHz, 60 kHz, 120 kHz or higher. Preferably, a frequency of 60-120 kHz or higher is used to atomize the solution of the bioabsorbable elastomer to the greatest possible extent so as to promote the formation of a smooth, uniform coating. Power can be controlled by adjusting the output level on the power supply. The nozzle power can be set at any suitable level, but is preferably about 0.9-1.2 W and more preferably about 1.0-1.1 W. The nozzle body can be fabricated from any suitable material, including titanium because of its good acoustical properties, high tensile strength, and excellent corrosion resistance. Liquid introduced onto the atomizing surface through a large, non-clogging feed tube running the length of the nozzle absorbs some of the vibrational energy, setting up wave motion in the liquid on the surface. For the liquid to atomize, the vibrational amplitude of the atomizing surface can be maintained within a band of input power to produce the nozzle's characteristic fine, low velocity mist. Since the atomization mechanism relies only on liquid being introduced onto the atomizing surface, the rate at which liquid is atomized depends largely on the rate at which it is delivered to the surface. Therefore, an ultrasonic nozzle can have a wide flow rate range. The maximum flow rate and median drop diameter corresponding to particular nozzle designs can be selected as design parameters by one skilled in the art. Preferably, the flow rate is between about 0.01-2.00 mL/min, more preferably between about 0.05-1.00 and most preferably between about 0.05-0.07 mL/min. Preferred coating parameters for USD using a Sono-tek Model 8700-60 ultrasonic nozzle are provided in Table 7 below:

TABLE 7

Ultrasonic Spray Deposition Parameters for Sono-tek Model 8700-60

| Flow rate (mL/min) | Coating velocity (in/sec) | Rotation Speed (rpm) | Nozzle Power (watts) | Process Gas (psi) | Distance (mm) |
| --- | --- | --- | --- | --- | --- |
| 0.01-2 | 0.01-0.5 | 30-150 | 0.9-1.2 | 0.1-2.5 | 1-25 |

Alternatively, the lubricious polymer coating can be dissolved in a solvent(s) and sprayed onto the medical device using a conventional spray gun such as a spray gun manufactured by Badger (Model No. 200), an electrostatic spray gun, or most preferably an ultrasonic nozzle spray gun. Medical device coatings comprising a taxane therapeutic agent may be applied to a surface of a medical device using a spray gun. The surface of the medical device can be bare, surface modified, or a primer coating previously applied to the medical device. The PEG or other polymer, can be dissolved in a solvent(s) and sprayed onto the medical device under a fume hood using a conventional spray gun, such as a spray gun manufactured by Badger (Model No. 200), or a 780 series spray dispense valve (EFD, East Providence, R.I.). Alignment of the spray gun and stent may be achieved with the use of a laser beam, which may be used as a guide when passing the spray gun over the medical device(s) being coated.

The distance between the spray nozzle and the nozzle size can be selected depending on parameters apparent to one of ordinary skill in the art, including the area being coated, the desired thickness of the coating and the rate of deposition. Any suitable distance and nozzle size can be selected. For example, for coating an 80 mm long stent, a distance of between about 1-7 inches between the nozzle and stent is preferred, depending on the size of the spray pattern desired. The nozzle diameter can be, for example, between about 0.014-inch to about 0.046-inch.

In one particular embodiment, a method of manufacturing a coated stent graft endoluminal therapeutic agent delivery system comprises the steps of: providing a solution comprising a solvent, a graft polymer and a therapeutic agent; evaporating the solvent from the solution to form a graft material comprising the graft polymer and the therapeutic agent, the graft material being adapted to release the therapeutic agent in an elution medium; attaching the graft material to a radially-expandable frame adapted for implantation within a body vessel to form a stent graft having an abluminal side and a luminal side defining a substantially cylindrical lumen and being movable from a radially expanded configuration to a radially compressed configuration; and applying a lubricious polymer to the abluminal side of the stent graft to form a coated stent graft endoluminal therapeutic agent delivery system having a coating of the lubricious polymer over at least a portion of the graft material.

8. Medical Device Delivery and Methods of Treatment

The medical devices as described herein can be delivered to any suitable body vessel, including a vein, artery, biliary duct, ureteral vessel, body passage or portion of the alimentary canal. Methods for delivering a medical device as described herein to any suitable body vessel are also provided, such as a vein, artery, biliary duct, ureteral vessel, body passage or portion of the alimentary canal. While many preferred embodiments discussed herein discuss implantation of a medical device in a vein, other embodiments provide for implantation within other body vessels. In another matter of terminology there are many types of body canals, blood vessels, ducts, tubes and other body passages, and the term "vessel" is meant to include all such passages.

One method of deploying the stent graft in a vessel involves radially compressing and loading the frame into a delivery device, such as a catheter. A restraining means may maintain the stent graft in the radially compressed configuration. For example, a self-expanding stent graft may be retained within a slidable sheath, while stent grafts that are not self-expanding may be crimped over a balloon portion of a delivery catheter. The compressed stent graft is thereby mounted on the distal tip of the delivery device, translated through a body vessel on the delivery device, and deployed from the distal end of the delivery device. For example, a delivery device may be a catheter comprising a pushing member adapted to urge the stent graft away from the delivery catheter. A sheath may be longitudinally translated relative to the stent graft to permit the stent graft to radially self-expand at the point of treatment within a body vessel.

Figure 3A:
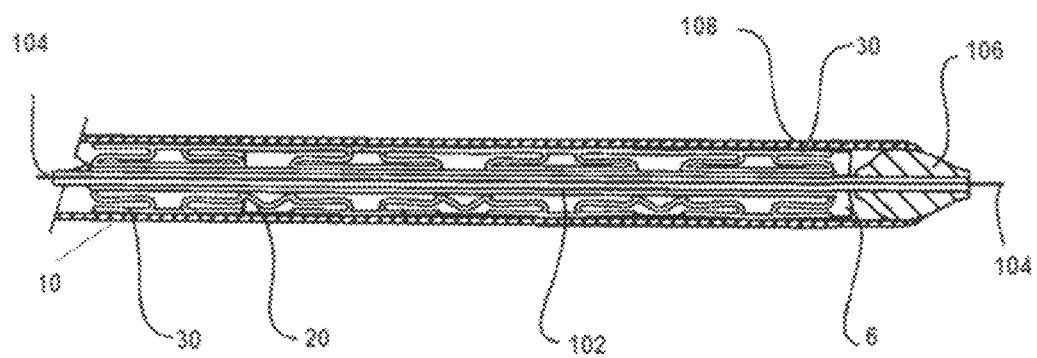
FIG. 3A is a side view of the implantable stent graft shown in FIG. 1 in a radially compressed configuration within the distal portion of a catheter delivery system.

Alternatively, a balloon may be inflated to radially expand the stent graft. FIG. 3A shows the stent graft 10 in a radially compressed configuration 10' in positioned in the distal portion of a catheter delivery system. The stent graft 10 includes the tubular graft 30 compressed around the radially compressed self-expanding support frame 20 around an inner lumen of the catheter that contains a wire guide 104. A retractable sheath 108 is disposed around the stent graft 10, maintaining the stent graft 10 in the radially compressed state 10'. A tapered distal portion 106 of the catheter is configured for translation of the catheter through a body vessel over the wire guide 104. At the site of implantation, the sheath 108 is translated away from the distal portion 106 of the catheter, permitting the support frame 20 to radially self expand toward the wall of the body vessel, deploying the stent graft.

Figure 3B:
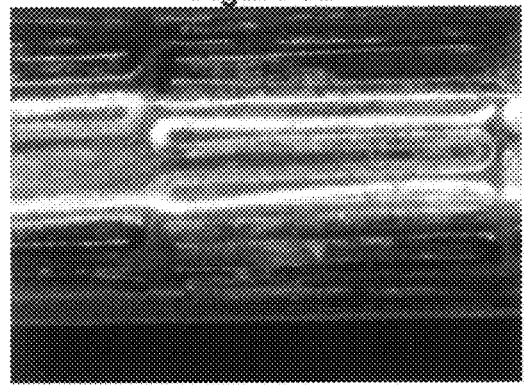
FIG. 3B is an image of a first paclitaxel-releasing stent graft coated with a lubricious coating.

FIG. 3B is an optical image a first paclitaxel-releasing stent graft coated with a lubricious coating in a radially-compressed configuration. The stent graft is formed from a paclitaxel-containing a modified biocompatible polyurethane polymer (sold under the tradename THORALON) applied to the luminal and abluminal surfaces of a radially expandable stent having an expanded diameter of 10 mm and a length of 40 mm. The graft was formed by spray coating a mandrel as described in Example 3 to form a graft having an inner portion on the luminal side of the stent adhered to an outer portion adhered to the abluminal side of the stent. The inner portion was formed by spray coating a first solution comprising the modified polyurethane in a volatile solvent without paclitaxel onto a mandrel, allowing the sprayed first solution to dry on the mandrel to form an inner layer of the inner portion, and then spray coating a second solution comprising the modified polyurethane and volatile solvent from the first solution and paclitaxel. After the spray coated second solution dried to form an outer layer of the inner portion, a radially-expandable stent having a plurality of openings in the outer wall in communication with an inner lumen was placed around the coated mandrel in a radially expanded configuration. The second solution was spray coated over the stent and dried to form an inner layer of an outer portion of the graft. Portions of the inner layer of the outer portion positioned over openings in the stent bonded to the outer layer of the interior portion through the stent openings, joining the exterior and interior portions of the graft. An intermediate layer of the second solution was spray coated over the inner layer of the outer portion, and an outer layer of the first solution was then spray coated over the intermediate layer of the outer portion to form a final graft structure formed by depositing a total of five layers. The outer layer of the outer portion was coated with a total of 14 mg of PEG (Mn=1000) and the resulting coated stent graft was crimped (radially compressed) to form the stent graft shown in FIG. 3B.

Figure 3C:
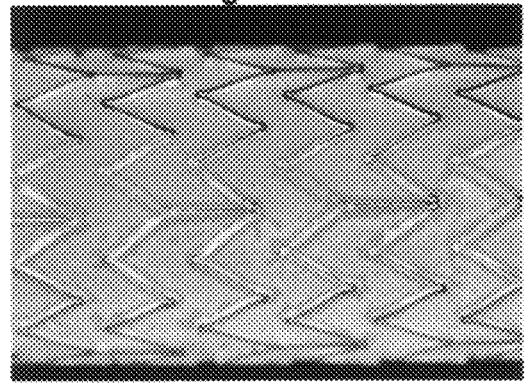
FIG. 3C is an image of a second paclitaxel-releasing stent graft coated with a lubricious coating.

FIG. 3C is an optical micrograph of another PEG-coated stent graft formed from the first solution above (i.e., the modified polyurethane sold under the tradename THORALON and a volatile solvent without paclitaxel). The graft was formed from an interior portion formed from three layers of the first solution and an exterior portion formed from three layers of the first solution (the paclitaxel-containing second solution was not used). A total of about 10 mg PEG (Mn=1000) was coated on the outer layer of the outer portion to form the stent graft shown in FIG. 3C. The stent graft is shown in a radially expanded configuration.

A third embodiment provides methods of treating a subject, which can be animal or human, comprising the step of implanting one or more medical devices as described herein. Methods of treatment preferably comprise the step of implanting one or more stent grafts configured to release a therapeutic agent, as described herein. In some embodiments, methods of treating may also include the step of delivering a stent graft to a point of treatment in a body vessel, or deploying a medical device at the point of treatment.

The stent graft can be delivered to a point of treatment within a body vessel in any suitable manner, Preferably, the endolumenal medical device is delivered percutaneously. For example, a biliary stent graft can be inserted into a biliary lumen in one of several ways: by inserting a needle through the abdominal wall and through the liver (a percutaneous transhepatic cholangiogram or "PTC"), by cannulating the bile duct through an endoscope inserted through the mouth, stomach, and duodenum (an endoscopic retrograde cholangiogram or "ERCP"), or by direct incision during a surgical procedure. A preinsertion examination, PTC, ERCP, or direct visualization at the time of surgery may be performed to determine the appropriate position for stent graft insertion. A wire guide can then be advanced through the lesion; a delivery catheter is passed over the wire guide to allow the stent graft to be inserted. In general, stent grafts are placed using a pusher tube over a wire guide with or without a guiding catheter. Delivery systems are now available for stent grafts that combine the guiding and pusher catheters (OASIS, Wilson-Cook Medical Inc., Winston-Salem, N.C.). The stent graft may be placed in the biliary duct either by the conventional pushing technique or by mounting it on a rotatable delivery catheter having a stent graft engaging member engageable with one end of the stent graft. Typically, when the diagnostic exam is a PTC, a wire guide and delivery catheter may be inserted via the abdominal wall. If the original exam was an ERCP, the stent graft may be placed via the mouth. The stent graft may then be positioned under radiologic, endoscopic, or direct visual control at a point of treatment, such as across the narrowing in the bile duct. The stent graft may be released using the conventional pushing technique. The delivery catheter may then be removed, leaving the stent graft to hold the bile duct open. A further cholangiogram may be performed to confirm that the stent graft is appropriately positioned.

Figure 4A:
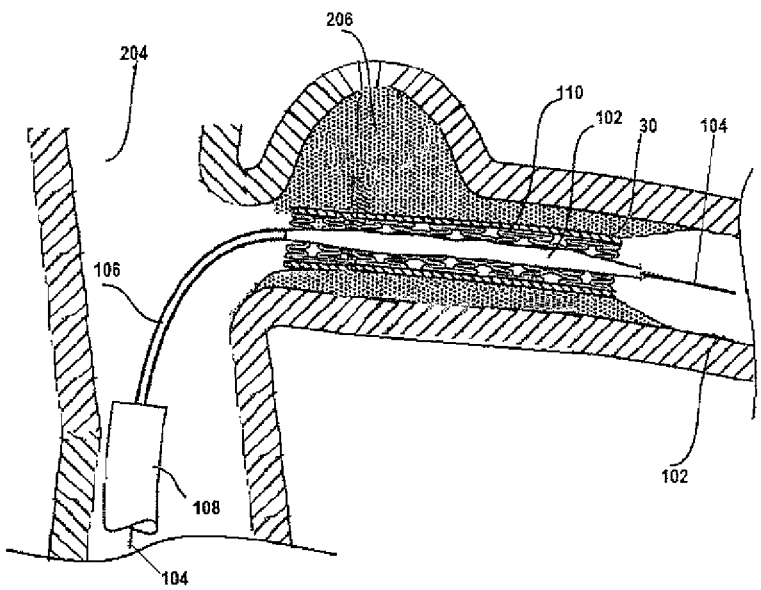
FIG. 4A shows placement of a balloon-expandable implantable stent graft within a biliary duct.
Figure 4B:
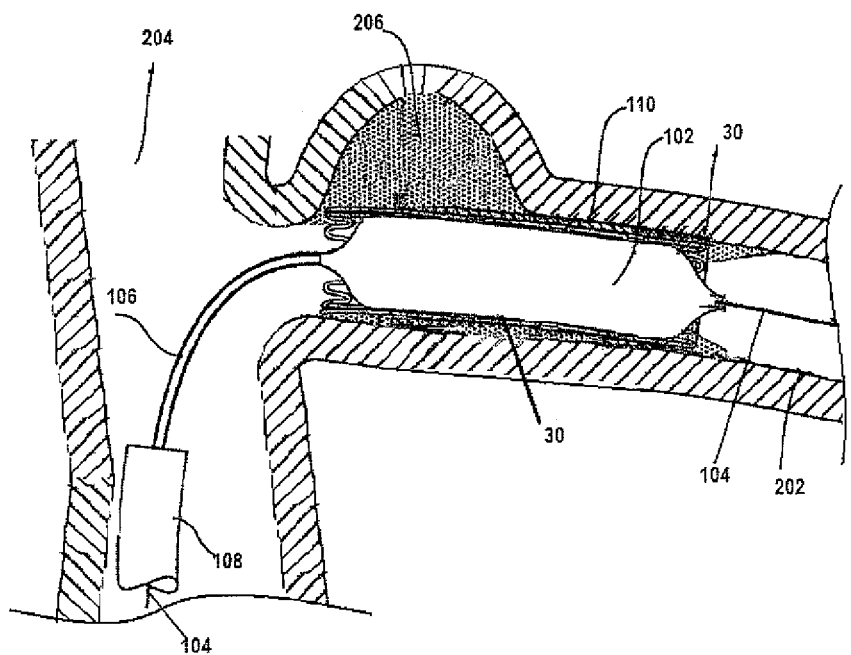
FIG. 4B shows the radial expansion of the implantable stent graft shown in FIG. 4A.
Figure 4C:
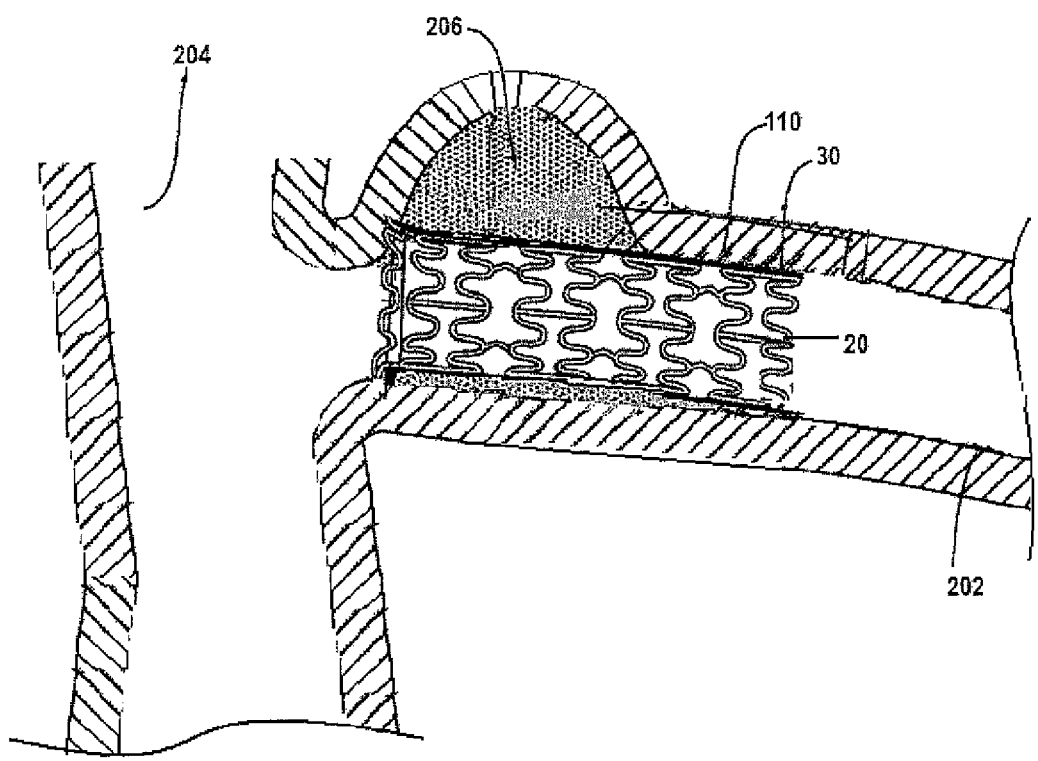
FIG. 4C shows the radially-expanded stent graft shown in FIGS. 4A-4B within the biliary duct.

For example, a stent graft may be advanced along the wire guide in a catheter, preferably by a pushing action from positioner located around the wire guide. FIGS. 4A-4C show an exemplary method of delivering a balloon expandable stent graft 110 comprising a balloon expandable (e.g., stainless steel) frame 20 attached to a tubular graft material 30 in a biliary duct 202 (or bile duct) using the wire guide. The stent graft 110 and wire guide assembly shown in FIGS. 4A-4C may be introduced to the duodenum 204 by any standard endoscopic technique for accessing the biliary duct 202, such as using a delivery catheter 108. The catheter 108 may be introduced via the oral cavity into the duodenum 204 to visualize the Papilla of Vater and Sphincter of Oddi, which lie at the opening to the common bile duct 202 and the pancreatic duct. In one exemplary method, the stent graft 110 and wire guide 104 are advanced from the accessory channel of the catheter 108 to cannulate a portion of the biliary duct 202. As shown in FIG. 4A, the wire guide 104 is advanced to a point of treatment within the biliary duct 202, and the distal portion of the catheter 106 is advanced over the wire guide 104. For applications where the size of the scope channel is restricted or other applications where there is limited room to accommodate both devices side by side, the drainage stent 110 can be modified to allow for the wire guide 104 to lie alongside without increasing the overall diameter. This can be done by forming an open channel (preferably one that would not capture the wire) or creating a flattened longitudinal portion along the length of the stent graft 110. The position of the biliary stent 110 may be monitored by detecting a radiopaque portion of the tubular member using standard imaging techniques. The biliary stent 110 is preferably placed at a site of treatment, such as the tumor 206 adjacent to the bile duct 202. As shown in FIG. 4B, the balloon 102 is inflated to radially expand the stent graft 110, bringing the graft 30 into contact with the tumor 206. The balloon 102 is deflated once the support frame 20 is radially expanded and the stent graft 110 secured in the bile duct 202, and the catheter 108 and wire guide 104 are removed. FIG. 4C shows the stent graft 110 in place within the bile duct 202, where a therapeutic agent is released from the covering layer for a desired period of time. The support frame 20 retains a resilient tubular shape to maintain patency of the bile duct, while the covering material reduces ingrowth of the surrounding tissue into the lumen of the stent graft 110.

In another particular embodiment, a method of treating a biliary tumor comprising the steps of: (1) providing a coated stent graft comprising a releasable therapeutic agent, the coated stent graft formed by the steps of: providing a solution comprising a solvent, a graft polymer comprising a polyurethane, and a taxane therapeutic agent; evaporating the solvent from the solution to form a graft material comprising the graft polymer and the therapeutic agent, the graft material being adapted to release the therapeutic agent in an elution medium; attaching the graft material to a radially-expandable frame adapted for implantation within a body vessel to form a stent graft having an abluminal side and a luminal side defining a substantially cylindrical lumen and being movable from a radially expanded configuration to a radially compressed configuration; and applying a lubricious polymer coating comprising pol(ethylene glycol) to the abluminal side of the stent graft to form the coated stent graft; (2) intralumenally inserting the coated stent graft into the blood vascular system using a means for intralumenal delivery comprising a catheter; (3) positioning the coated stent graft within a biliary duct; and (4) radially expanding the coated stent graft within the biliary duct so as to place the graft in contact with a portion of a wall of the biliary duct in a manner effective to deliver the therapeutic agent to the wall of the biliary duct.

INDUSTRIAL APPLICABILITY

Among other applications, the present invention can be used for providing a medical implantable device such as a stent graft within a human or veterinary patient, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention, It is also to be understood that the invention is directed to embodiments both comprising and consisting of the disclosed parts.

EXAMPLES

Example 1

Compositions for Coating a Support Frame with a Non-Porous THORALON Biocompatible Polyurethane A solution for spray coating non-porous polyureaurethane (e.g., such as a product sold under the tradename THO-RALON) can be made by mixing 25 g of a solid mixture containing polyetherurethane urea (BPS-215) and 2% wt of the surface modifying additive (SMA-300) in dimethyacetamide (DMAC) solvent for a total solution weight of 100 g. The solution has a viscosity of less than about 2,000 Cp. The entire composition can be cast as a sheet, or coated onto an article such as a mandrel or a mold. To prepare a solution for spray coating porous polyureaurethane, the micronized (ca. 25 mm) sodium chloride salt in an amount equal to about six times the total solid weight of the BPS-215 and SMA-300 components can be added to the solution.

A solution for dip coating non-porous polyureaurethane can be made by mixing 25 g of a solid mixture containing polyetherurethane urea (BPS-215) and 5% wt of the surface modifying additive (SMA-300) in dimethyacetamide (DMAC) solvent for a total solution weight of 100 g. The solution has a viscosity of about 2,000-3,000 Cp. To prepare a solution for spray coating porous polyureaurethane (e.g., THORALON), the micronized (ca. 25 mm) sodium chloride salt may be included in an amount equal to about six times the total solid weight of the BPS-215 and SMA-300 components added to the solution. The entire composition can be cast as a sheet, or coated onto an article such as a mandrel or a mold.

Example 2

Cast Coating to Form a THORALON Biocompatible Polyurethane Sleeve

A tubular sleeve of polyureaurethane material (e.g., THORALON) attached to a series of coaxially-aligned hoop members was prepared. The following steps were followed to form an implantable stent graft:

about 10 mL of a polyureaurethane-DMAC (THORALON/DMAC polyurethane) solution was prepared with a weight ratio of solid (BPS-215 and SMA-300, and optionally containing a salt for forming the porous THORALON material) to DMAC of between about 1:1.5 to about 2:1;

a glass tube was cleaned with soap and water, and about 2 mL of the solution was applied uniformly to the inside of the glass tube;

the coated glass tube was heated while rotating the tube slowly about the longitudinal axis (ca. 5 rpm) for about 2 hours at about 40° C.;

the coated glass tube is cooled to room temperature and multiple self-expanding hoop members were deployed within the coated glass tube;

about 2 mL of the solution was applied uniformly to the inside of the glass tube and around the hoop members;

the coated glass tube and hoop members was heated while rotating the tube slowly about the longitudinal axis (ca. 5 rpm) for about 2 hours at about 40° C.;

the dried sleeve structure containing the hoop members was removed from the glass tube and soaked in a warm water bath at a temperature of about 65° C. for about 1 hour, then removed and dried; and a sinusoidal hoop member was radially compressed and deployed within the lumen of the outer sleeve to form a stent graft.

Example 3

Paclitaxel-Eluting Thoralon Stent Grafts

Stent grafts comprising paclitaxel in a multi-layer polyureaurethane stent graft were prepared using various solutions having the compositions described in Table 8 below. A polyureaurethane stock solution is made up of 11.75% THORALON solids and 88.25% dimethylacetamide DMAc (dimethylacetamide). Non-porous polyureaurethane material was designated "skin" while porous polyureaurethane material was designated "foam." Solutions for forming skin polyureaurethane materials with paclitaxel ("TSkPTX") and without ("TSk") paclitaxel were made, as well as solutions for forming foam polyureaurethane materials with ("TFPTX") and without ("TF") paclitaxel. Paclitaxel is used as a preferred example to illustrate that any polyurethane material can be loaded with any suitable drug.

Preparing Thoralon Skin Solutions:

To prepare a solution suitable for forming a non-porous polyureaurethane ("skin solution"), thirty grams of DMAc was added to thirty grams polyureaurethane (e.g., THORALON) stock solution. The solution was mixed for 45 minutes. After mixing, the solution is degassed in a vacuum system. A skin solution comprising paclitaxel ("TSkPTX") was separately prepared. When preparing a TSkPTX solution, thirty grams of 50 mM PTX in DMAc was added to the Thoralon stock solution, mixed and degassed.

Preparing Thoralon Foam Solutions:

To prepare Thoralon foam-only solution, 0.1597 g SAG 100 and 0.399 g SMA 300 were added to thirty grams of DMAc. Solution was mixed on reciprocal mixer for five minutes. The solution was then added to 32.6 g Thoralon stock solution and mixed for 30 minutes. During mixing, 47.93 g salt was gradually added to solution over the thirty minute mixing time. Mixing then continued for an additional 45 minutes. After mixing, solution was degassed. (This solution is good for up to three days, and when not in use, is kept on a rotating wheel to prevent salt from falling out of solution.) When preparing a TFPTX solution, thirty grams of 50 mM PTX in DMAc was used in place of DMAc.

TABLE 8

Percent composition of solutions:

|  | Thoralon solids | DMAc | PTX | SMA-300 | SAG-100 | Salt |
|---|---|---|---|---|---|---|
| TSk | 11.75 | 88.25 | — | — | — | — |
| TSk$^{PTX}$ | 11.75 | 85.98 | 2.27 | — | — | — |
| TF | 6.44 | 52.79 | — | 0.34 | 0.13 | 40.30 |
| TF$^{PTX}$ | 6.44 | 51.64 | 1.15 | 0.34 | 0.13 | 40.30 |

Spraying:

An airbrush spray gun was loaded with a polyureaurethane/DMAC solution and calibrated to spray 1 mL/min. A 10 mm diameter glass mandrel was inserted into chuck. A mandrel was preheated for three minutes when spraying a skin solution described above. While spraying the solution, the gun was translated with a traverse speed of the gun is 5 mm/sec along the mandrel, and the mandrel was rotated with a rotational speed of the mandrel of 30 rpm. The mandrel was left to dry for nine minutes between coats. After final coat, the mandrel was dried for one hour over heat. The spray compositions in Table 8 were applied to the mandrel.

Multiple coats were sprayed on the mandrel to form an inner portion (36). Stents (20) were then loaded onto inner portion (36) coats and a series of abluminal coats were sprayed in the same manner described above to form the outer portion 34 of the graft 30.

After spraying, mandrels are placed in a 60° C. water bath for six hours. After six hours, mandrels were removed from water bath and stents are removed from mandrels. Stents are then placed in oven at 60° C. for 48 hours. After removing stents from oven, edges of coating are trimmed.

Coating Formulations

A series of 10 mm (radially expanded diameter)×40 mm (length) tubular radially-expanding ZILVER (Cook Inc., Bloomington, Ind.) self expanding NITINOL stents were spray coated on a mandrel (20), as described above, using three different coating formulations. The layers on the lumen are the Inner Diameter layers (ID) and those on the abluminal surface are the Outer Diameter layers (OD). The coating formulations are depicted as (TFn; TSkn//TSknPTX; TFn), where the stent (//), the outer portion (34) is represented by layers described to the right of the "//" symbol and the inner portion (36) is described by the layers to the left of the "//" symbol, and n indicates the number of layers. If the layer contains PTX, it is denoted by a superscript. Optionally, a layer of PEG (32) with Mn=1,000 was applied to the outer portion (34).

To determine the rate at which the paclitaxel elutes, stent grafts (30) were placed in 0.5% sodium dodecyl sulfate (SDS) while being sonicated. The doses were determined by the last UV-Vis reading, as described above. FIGS. 2A-2D show elution profiles obtained from various graft configurations, as described above.

Tables 9 and 10 show data obtained from a series of stent grafts formed from a four layer graft with the configuration: $TF_1^{PTX}$: $TSk_3^{PTX}$//$TSk_5^{PTX}$: $TF_5^{PTX}$ where "//" indicates the position of the support frame between the luminal (inner portion, 36) (far left) and the abluminal (outer portion, 34) surface (far right). The elution rates for Structure B and Structure C at a total paclitaxel dose of about 8-11 mg for Structure B and about 21-26 mg for Structure C varied with temperature. At a given amount of paclitaxel in a stent graft, the elution rate was slower (and the time required to elute 80% wt of the paclitaxel from the stent graft was longer) at 37° C. than at room temperature (25° C.) for both Structure B and Structure C. Increasing the temperature from room temperature to 37° C. unexpectedly decreased the elution rate, rather than increasing the elution rate. In addition, increasing the temperature to 60° C. resulted in measured elution rates for both structure B and structure C that were considerably faster than the elution rates measured at both room temperature and at 37° C.

TABLE 9

Comparison of elution rates of different PTX/Thoralon formulations in 0.5% SDS

| Structure | Sample | Temperature | Time to 80% Elution (hrs) | Dose (mg) |
|---|---|---|---|---|
| A | 1 | 60° C. | 6.5 | 17 |
| A | 2 | 60° C. | 6.9 | 17 |
| A | 3 | 60° C. | 3.2 | 11 |
| B | 4 | 60° C. | 4.5 | 11 |
| B | 5 | room temp | 71.2 | 8 |
| B | 6 | 37° C. | 95.5 | 8 |
| C | 7 | 60° C. | 9.4 | 26 |
| C | 8 | 37° C. | 95.5 | 21 |
| C | 9 | room temp | 67.0 | 22 |

TABLE 10

Weights of Coatings and Doses PTX PTX/Coating Ratios

| Structure | Sample | Gravimetric Coating Weight (Thoralon + drug) (mg) | PTX Dose by UV-Vis (mg) | Average PTX Dose (mg) | % of Coating that is made up of PTX | Std Dev |
|---|---|---|---|---|---|---|
| A | 1 | 125 | 17 | 15 | 13.6 | 0.7 |
|   | 2 | 140 | 17 |    | 12.1 |     |
|   | 3 | 88  | 11 |    | 12.5 |     |
| B | 4 | 172 | 11 | 9  | 6.4  | 0.7 |
|   | 5 | 147 | 8  |    | 5.4  |     |
|   | 6 | 161 | 8  |    | 5.0  |     |
| C | 7 | 180 | 26 | 22 | 14.4 | 1.8 |
|   | 8 | 181 | 21 |    | 11.6 |     |
|   | 9 | 162 | 22 |    | 11.1 |     |

Example 4

Applying PEG Coating to Drug-Eluting THORALON Stent Grafts

Stent graft structures made according to Example 3 were coated with a polyethylene glycol (PEG) coating (32) applied to the abluminal surface of the graft. PTX/Thoralon coated Zilver stent grafts with a radially expanded diameter of 10 mm and a length of 40 mm were coated with polyethylene glycol (PEG) via ultrasonic spraying. PEG is soluble in water and comes off the stent during elutions in 0.5% aqueous SDS. The PEG coating (32) was lubricious enough to allow the stent to slide through the crimping device and into the delivery system without tearing or otherwise compromising the integrity of the graft (30) material. With at least 7 mg PEG applied to a 10×40 mm PTX/Thoralon stent, the stent was also easily deployed.

Several 10×40 mm PTX/Thoralon coated stent grafts were coated with 8 g/L PEG (Mn=1000) in dichloromethane via ultrasonic coating. The stent was ultrasonically spray coated using the following parameters:

TABLE 11

Coating Parameters for PEG

| | |
|---|---|
| Nozzle power: | 1.1 watts |
| Distance from nozzle to stent: | 11 mm |
| Rotation Speed: | 110 rpm |
| Flow rate: | 0.06 mL/min |
| Translational speed: | 0.050 in/sec |
| Air shroud pressure: | 1.5 psi |
| Humidity: | 9.0-9.4% |
| Temperature: | 77.3-78.7° F. |
| Loops: | 20 |

The average dose of PEG was 9 mg. The stents were then crimped and loaded into 6 Fr delivery systems. The stent and a gauge pin were crimped with a push rod using the crimping device. The push rod, which is smaller than the gauge pin, is then used to push the gauge pin, which in turn pushes the stent into the delivery system without being pushed into the stent. The delivery system has the inner sheath removed and replaced with a wire guide. After crimping and loading, the stents were deployed into trace clean vials. The stents were weighed, and there was an average weight loss of 2.7 mg PEG.

TABLE 12

PEG Doses Before and After Crimping

| Stent | Dose PEG (mg) | Weight w/PEG (mg) | Weight after crimping (mg) | Difference (mg) |
|---|---|---|---|---|
| 2  | 6.7  | 223.5  | 225.4  | 1.9  |
| 4  | 8.9  | 223.20 | 220.30 | -2.90 |
| 6  | 8.5  | 224.10 | 221.80 | -2.30 |
| 9  | 8.4  | 206    | 202    | -4   |
| 10 | 8.4  | 191    | 190    | -1   |
| 11 | 8.6  | 188.3  | 185.5  | -2.8 |
| 12 | 10.5 | 189.6  | 188.1  | -1.5 |
| 13 | 12.2 | 190.6  | 186.5  | -4.1 |
| 17 | 8.8  | 205.4  | 202.6  | -2.8 |

Table 13 includes the weight of paclitaxel and PEG for other 10 mm (expanded outer diameter)×40 mm (length) stent grafts prepared according to Example 3 and coated with various lubricious PEG polymer coatings as described above in Example 4. Table 13 also includes the calculated dose of paclitaxel and PEG (Mn=1,000) in micrograms/mm$^2$ abluminal surface area, and the weight ratio of paclitaxel to PEG. The 10×40 mm stents were coated with about 2.5, 5, 7 and 10 mg PEG. Stent grafts coated with only 2.5 mg PEG and a weight ratio of paclitaxel:PEG of 3.60, 6.00 and 8.80 could be loaded but not deployed without damage to the stent graft (See Table 13). Some stent grafts with 5 mg PEG could be deployed, but not all. Stent grafts with either 6.7 or 10.5 mg PEG and weight ratios of paclitaxel to PEG of about 1.34 to 3.28 could be easily deployed without damage to the stent (See Table 13). Notably, coated stent grafts having a paclitaxel to PEG weight ratio of less than about 3.60, including ratios of 0.74-3.28, could be successfully deployed from the 6-French delivery system. Coated stent grafts with paclitaxel to PEG weight ratios in excess of about 3.6, including ratios of 3.6-8.8, were more difficult to deploy without damage to the graft material, which could result in physical deformation of the graft material. Such physical damage could include folds or tears in the material resulting in possible loss of the paclitaxel during deployment and/or alteration of the elution rate of the paclitaxel after deployment.

TABLE 13

| Stent Diameter | Stent Length | Abluminal Surface Area of Outer Layer of Outer Portion of Stent Graft | Total weight of paclitaxel in graft (mg) | Total weight of PEG (Mn = 1000) in outer coating (mg) | Dose of paclitaxel in stent graft (micrograms/mm$^2$) | Dose of PEG outer coating on stent graft (micrograms/mm$^2$) | Weight Ratio of Paclitaxel: PEG (mg: mg) |
|---|---|---|---|---|---|---|---|
| 10 | 40 | 1256 | 9  | 12.2 | 7.17  | 9.71 | 0.74 |
| 10 | 40 | 1256 | 9  | 10.5 | 7.17  | 8.36 | 0.86 |
| 10 | 40 | 1256 | 9  | 8.5  | 7.17  | 6.77 | 1.06 |
| 10 | 40 | 1256 | 15 | 12.2 | 11.94 | 9.71 | 1.23 |

TABLE 13-continued

| Stent Diameter | Stent Length | Abluminal Surface Area of Outer Layer of Outer Portion of Stent Graft | Total weight of paclitaxel in graft (mg) | Total weight of PEG (Mn = 1000) in outer coating (mg) | Dose of paclitaxel in stent graft (micrograms/ mm$^2$) | Dose of PEG outer coating on stent graft (micrograms/ mm$^2$) | Weight Ratio of Paclitaxel: PEG (mg: mg) |
|---|---|---|---|---|---|---|---|
| 10 | 40 | 1256 | 9 | 6.7 | 7.17 | 5.33 | 1.34 |
| 10 | 40 | 1256 | 15 | 10.5 | 11.94 | 8.36 | 1.43 |
| 10 | 40 | 1256 | 15 | 8.5 | 11.94 | 6.77 | 1.76 |
| 10 | 40 | 1256 | 22 | 12.2 | 17.52 | 9.71 | 1.80 |
| 10 | 40 | 1256 | 22 | 10.5 | 17.52 | 8.36 | 2.10 |
| 10 | 40 | 1256 | 15 | 6.7 | 11.94 | 5.33 | 2.24 |
| 10 | 40 | 1256 | 22 | 8.5 | 17.52 | 6.77 | 2.59 |
| 10 | 40 | 1256 | 22 | 6.7 | 17.52 | 5.33 | 3.28 |
| 10 | 40 | 1256 | 9 | 2.5 | 7.17 | 1.99 | 3.60 |
| 10 | 40 | 1256 | 15 | 2.5 | 11.94 | 1.99 | 6.00 |
| 10 | 40 | 1256 | 22 | 2.5 | 17.52 | 1.99 | 8.80 |

We claim:

1. A method of treating a biliary tumor comprising the steps of
   a. intralumenally inserting a radially expandable coated stent graft in a radially compressed configuration into a body vessel, the coated stent graft having an abluminal surface with a surface area and a luminal surface defining a drainage lumen, the coated stent graft having a graft material attached to a radially expandable support frame, and a coating comprising a poly(alkyl glycol) polymer on the abluminal surface of the graft material; the graft material containing a taxane therapeutic agent and a polyurethane polymer and forming at least a portion of both the luminal surface and the abluminal surface, the graft material formed from a polymer including polydimethylsiloxane and a polyurethane and further including about 5-100 micrograms of the taxane therapeutic agent per mm$^2$ of the surface area of the abluminal surface with a weight ratio of the taxane therapeutic agent to the poly(alkylene glycol) of between about 0.10 and 3.50;
   b. translating the stent graft within the body vessel to position the stent graft within a biliary duct proximate the biliary tumor; and
   c. radially expanding the stent graft within the biliary duct so as to place the stent graft in contact with a portion of a wall of the biliary duct in a manner effective to deliver the taxane therapeutic agent to the wall of the biliary duct.

2. The method of claim 1, further comprising the step of retaining at least 20%wt of the taxane therapeutic agent in the graft after 90 hours of contacting the abluminal surface with the wall of the biliary duct.

3. The method of claim 1, where the poly(alyl glycol) is poly(ethylene glycol).

4. The method of claim 1, where the graft material comprises a total of about 5-25 milligrams of the taxane therapeutic agent.

5. The method of claim 3, where the graft material comprises a total of 10-15 milligrams paclitaxel and about 3-60 micrograms paclitaxel per mm$^2$ of the abluminal surface area.

6. The method of claim 5, where the graft material comprises a total of 5-100 milligrams of the poly(ethylene glycol) and about 5-100 micrograms poly(ethylene glycol) per mm$^2$ of the abluminal surface area).

7. The method of claim 6, where the poly(ethylene glycol) has a weight average molecular weight in the range from 100 to about 10,000.

8. The method of claim 7, where increasing the total amount of the taxane therapeutic agent in the graft material increases the time required to elute 80% of the taxane therapeutic agent by weight from the graft material in vitro in a 0.5% aqueous SDS solution at 25° C.

9. The method of claim 8, where the graft material comprises a modified solid polymer blend formed of a base polymer comprising the polyurethane and a solid thermoplastic segmented block copolymer additive blended with the base polymer, the additive comprising a first essentially linear segmented copolymer chain and a second essentially linear polymer chain chemically bonded to said first segmented copolymer chain, said second polymer chain being selected from a polar homopolymer or a second segmented copolymer; said additive characterized by a ☐c less than said base polymer and said first segmented copolymer chain characterized by the presence of at least one polar hard segment having a glass transition temperature or crystalline melting temperature above 37° C., and a nonpolar soft block having a glass transition temperature or crystalline melting temperature below 37° C.; said second segmented copolymer or polar homopolymer characterized by the presence of at least one second polar hard segment having a glass transition temperature or crystalline melting temperature above 37° C., and said second segmented copolymer further characterized by the presence of a polar soft block having a glass transition temperature or crystalline melting temperature below 37° C., said polar hard segments independently selected from the group consisting of a polyurethane and a polyurethaneurea.

10. A coated tubular stent graft having an abluminal surface with a surface area and a luminal surface defining a drainage lumen, the coated stent graft comprising: a graft material attached to a radially expandable support frame to form at least a portion of both the luminal surface and the abluminal surface of the coated tubular stent graft and a coating including a glycol polymer on the portion of the graft material forming the abluminal surface, the graft material containing about 5-100 micrograms of a taxane therapeutic agent per mm$^2$ of the surface area of the abluminal surface and a polyurethane polymer comprising a polymer including polydimethylsiloxane and a polyurethane, the stent graft having a weight ratio of the taxane therapeutic agent to the glycol of between about 0.10 and 3.50.

11. The stent graft of claim 10, where increasing the total amount of the taxane therapeutic agent in the graft material increases the time required to elute 80% of the taxane therapeutic agent by weight from the graft material in vitro in a 0.5% aqueous SDS solution at 25° C.

12. The stent graft of claim 11, where increasing the temperature of the graft material from 25° C. to 37° C. increases the time required to elute 80% of the taxane therapeutic agent by weight from the graft material in vitro in a 0.5% aqueous SDS solution.

13. The stent graft of claim 10, where the glycol polymer is poly(ethylene glycol) with a weight average molecular weight in the range from 100 to about 10,000.

14. The stent graft of claim 10, where the graft material comprises a total of about 5-25 milligrams of the taxane therapeutic agent.

15. The stent graft of claim 14, where the graft material comprises a total of 10-15 milligrams paclitaxel and about 3-60 micrograms paclitaxel per mm$^2$ of the abluminal surface area.

16. The stent graft of claim 15, where the graft material comprises a total of 5-100 milligrams of the poly(ethylene glycol) and about 1-40 micrograms poly(ethylene glycol) per mm$^2$ of the abluminal surface area.

17. The stent graft of claim 16, where the weight ratio of the total paclitaxel to the total poly(ethylene glycol) is about 0.1 to 1.50.

18. A method of manufacturing a stent graft, the method comprising the steps of:
   a. forming a first solution comprising a taxane therapeutic agent, a polymer and a solvent, the concentration of the taxane therapeutic agent being less than about 400 mM in the first solution and the polymer including polydimethylsiloxane and at least one polymer selected from the group consisting of: polyurethane and polyureaurethane;
   b. contacting the first solution with a radially expandable support frame and drying at least a portion of the first solution contacting the support frame to form a graft material attached to the support frame to form an abluminal surface, the graft material containing about 5-100 micrograms of a taxane therapeutic agent per mm$^2$ of a surface area of the abluminal surface;
   c. applying a poly(alkyl glycol) polymer to the graft material to form a coating consisting essentially of the poly(alkylene glycol) on at least a portion of the graft material to form a coated stent graft having a weight ratio of the taxane therapeutic agent to the poly(alkyl glycol) of between about 0.10 and 3.50.

19. The method of claim 18, where the poly(alkyl glycol) is poly(ethylene glycol) having an average molecular weight of about 1,000 and where the graft material comprises a modified solid polymer blend formed of a base polymer comprising the polyurethane and a solid thermoplastic segmented block copolymer additive blended with the base polymer, the additive comprising a first essentially linear segmented copolymer chain and a second essentially linear polymer chain chemically bonded to said first segmented copolymer chain, said second polymer chain being selected from a polar homopolymer or a second segmented copolymer; said additive characterized by a □c less than said base polymer and said first segmented copolymer chain characterized by the presence of at least one polar hard segment having a glass transition temperature or crystalline melting temperature above 37° C., and a nonpolar soft block having a glass transition temperature or crystalline melting temperature below 37° C.; said second segmented copolymer or polar homopolymer characterized by the presence of at least one second polar hard segment having a glass transition temperature or crystalline melting temperature above 37° C., and said second segmented copolymer further characterized by the presence of a polar soft block having a glass transition temperature or crystalline melting temperature below 37° C., said polar hard segments independently selected from the group consisting of a polyurethane and a polyurethaneurea.

20. The method of claim 19, where the graft material comprises a total of 10-15 milligrams paclitaxel and about 3-60 micrograms paclitaxel per mm$^2$ of the abluminal surface area; and where the coating consists of about 5 to 15 milligrams of polyethylene glycol).

* * * * *

UNITED STATES PATENT AND TRADEMARK OFFICE
CERTIFICATE OF CORRECTION

PATENT NO. : 9,474,833 B2  
APPLICATION NO. : 11/958090  
DATED : October 25, 2016  
INVENTOR(S) : Patrick H. Ruane et al.

Page 1 of 1

It is certified that error appears in the above-identified patent and that said Letters Patent is hereby corrected as shown below:

In the Claims

In Column 42, Claim 20, about Line 39, after "milligrams of" replace "polyethylene glycol)." with --poly(ethylene glycol).--.

Signed and Sealed this  
Eighth Day of May, 2018

Andrei Iancu  
*Director of the United States Patent and Trademark Office*